(12) United States Patent
Shoshtaev et al.

(10) Patent No.: US 12,414,860 B2
(45) Date of Patent: Sep. 16, 2025

(54) IMPLANT WITH BONE SCREW RETENTION

(71) Applicant: LIFE SPINE, INC., Huntley, IL (US)

(72) Inventors: Eugene Shoshtaev, Del Mar, CA (US); Paul Christopher Zakelj, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 211 days.

(21) Appl. No.: 18/319,084

(22) Filed: May 17, 2023

(65) Prior Publication Data

US 2023/0285160 A1    Sep. 14, 2023

Related U.S. Application Data

(63) Continuation of application No. 16/734,232, filed on Jan. 3, 2020, now Pat. No. 11,672,674, which is a continuation-in-part of application No. 15/957,021, filed on Apr. 19, 2018, now Pat. No. 10,524,929.

(60) Provisional application No. 62/487,092, filed on Apr. 19, 2017.

(51) Int. Cl.
*A61F 2/44* (2006.01)
*A61B 17/88* (2006.01)
*A61F 2/30* (2006.01)

(52) U.S. Cl.
CPC ... *A61F 2/4455* (2013.01); *A61F 2002/30011* (2013.01); *A61F 2002/30143* (2013.01); *A61F 2002/30433* (2013.01)

(58) Field of Classification Search
CPC .......... A61F 2/4455; A61F 2002/30011; A61F 2002/30143; A61F 2002/30433

USPC ............ 623/17.11, 17.16; 606/246, 99, 295, 606/86 A

See application file for complete search history.

(56) References Cited

U.S. PATENT DOCUMENTS

| | | | |
|---|---|---|---|
| 9,161,842 B2 | 10/2015 | Chin et al. | |
| 9,775,722 B2 | 10/2017 | Kim et al. | |
| 11,672,674 B2 * | 6/2023 | Shoshtaev | ............ A61F 2/4611 623/17.16 |
| 2007/0250167 A1 | 10/2007 | Bray et al. | |
| 2008/0249569 A1 * | 10/2008 | Waugh | .................... A61F 2/447 606/249 |
| 2010/0305704 A1 | 12/2010 | Messerli et al. | |
| 2011/0230971 A1 | 9/2011 | Donner et al. | |
| 2012/0271423 A1 | 10/2012 | Wallenstein et al. | |
| 2012/0277870 A1 | 11/2012 | Wolters et al. | |

(Continued)

FOREIGN PATENT DOCUMENTS

| | | | | |
|---|---|---|---|---|
| CN | 103068343 A | * | 4/2013 | ............ A61B 17/70 |
| EP | 3 052 037 A1 | | 8/2016 | |

(Continued)

OTHER PUBLICATIONS

Machine translation of CN 103068343 A (Year: 2013).*

(Continued)

*Primary Examiner* — Eduardo C Robert
*Assistant Examiner* — David C Comstock
(74) *Attorney, Agent, or Firm* — Foley & Lardner LLP

(57) ABSTRACT

An implant includes an interbody device having a front, a rear, a first lateral side, a second lateral side, a central cavity, and a plurality of bores extending into the rear of the interbody device, each arced bore being configured to receive an arced anchoring member.

20 Claims, 34 Drawing Sheets

(56) References Cited

U.S. PATENT DOCUMENTS

| | | |
|---|---|---|
| 2013/0073044 A1 | 3/2013 | Gamache |
| 2013/0166029 A1 | 6/2013 | Dinville et al. |
| 2013/0226300 A1 | 8/2013 | Chataigner et al. |
| 2014/0046448 A1 | 2/2014 | Kana et al. |
| 2014/0107786 A1* | 4/2014 | Geisler .................. A61F 2/447 623/17.16 |
| 2015/0209089 A1 | 7/2015 | Chataigner et al. |
| 2015/0238324 A1 | 8/2015 | Nebosky et al. |
| 2015/0328005 A1 | 11/2015 | Padovani et al. |
| 2016/0008140 A1 | 1/2016 | Melkent et al. |
| 2016/0151171 A1 | 6/2016 | Mozeleski et al. |
| 2017/0020685 A1 | 1/2017 | Geisler et al. |
| 2017/0056203 A1 | 3/2017 | Gray et al. |
| 2017/0224502 A1 | 8/2017 | Wolters et al. |
| 2017/0333205 A1 | 11/2017 | Joly et al. |
| 2018/0256336 A1 | 9/2018 | Mueller et al. |
| 2018/0303623 A1 | 10/2018 | Shoshtaev |
| 2019/0000638 A1* | 1/2019 | Gilbride .................. A61F 2/447 |
| 2019/0117408 A1 | 4/2019 | Willis et al. |

FOREIGN PATENT DOCUMENTS

| | | |
|---|---|---|
| WO | WO-2010/054181 A1 | 5/2010 |
| WO | WO-2019/006476 A | 1/2019 |

OTHER PUBLICATIONS

International Search Report and Written Opinion for PCT/US2018/028278, dated Jun. 21, 2018.

Notice of Allowance on U.S. Appl. No. 16/734,232 dtd Jan. 30, 2023.

PCT Preliminary Report on Patentability for International Application No. PCT/US2018/028278 mailing date Oct. 31, 2019, 12 pages.

* cited by examiner

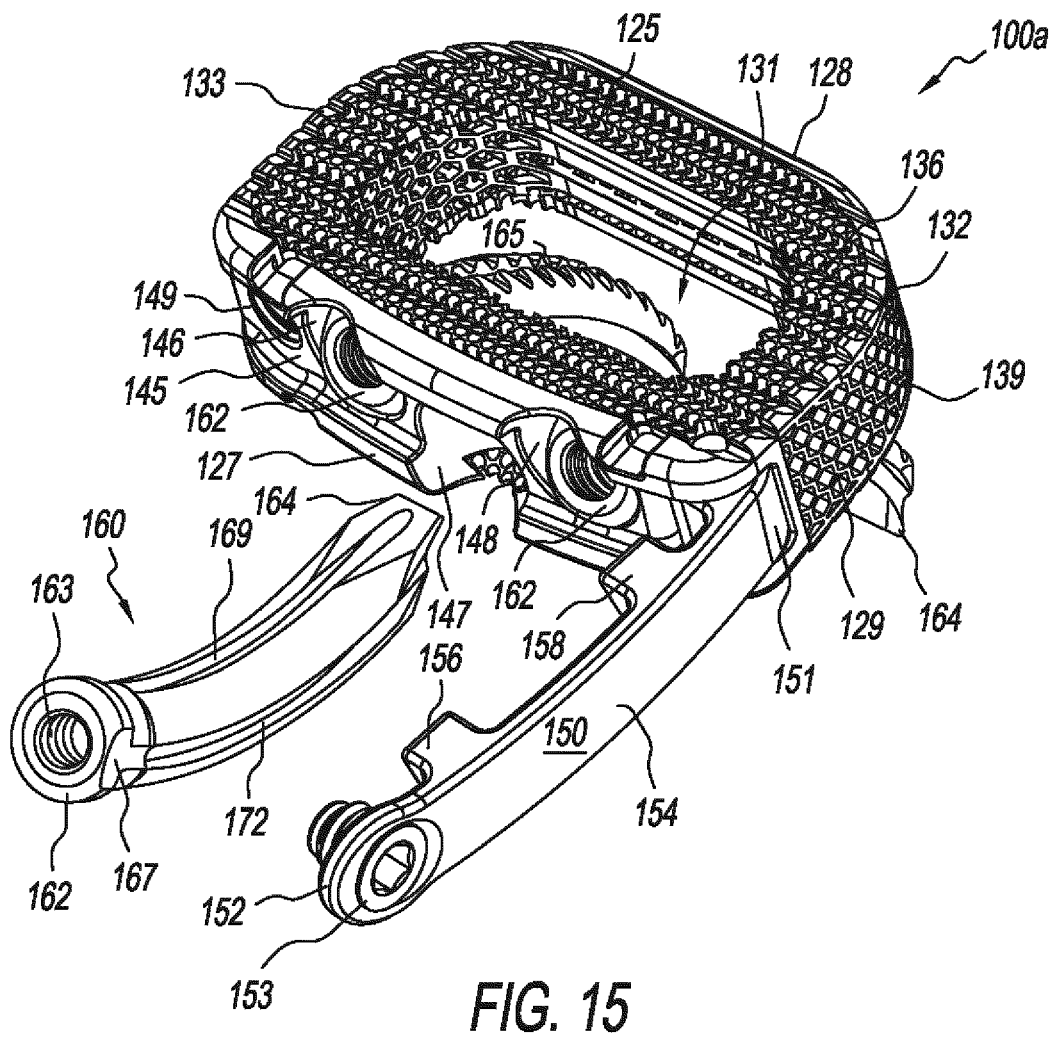
FIG. 15
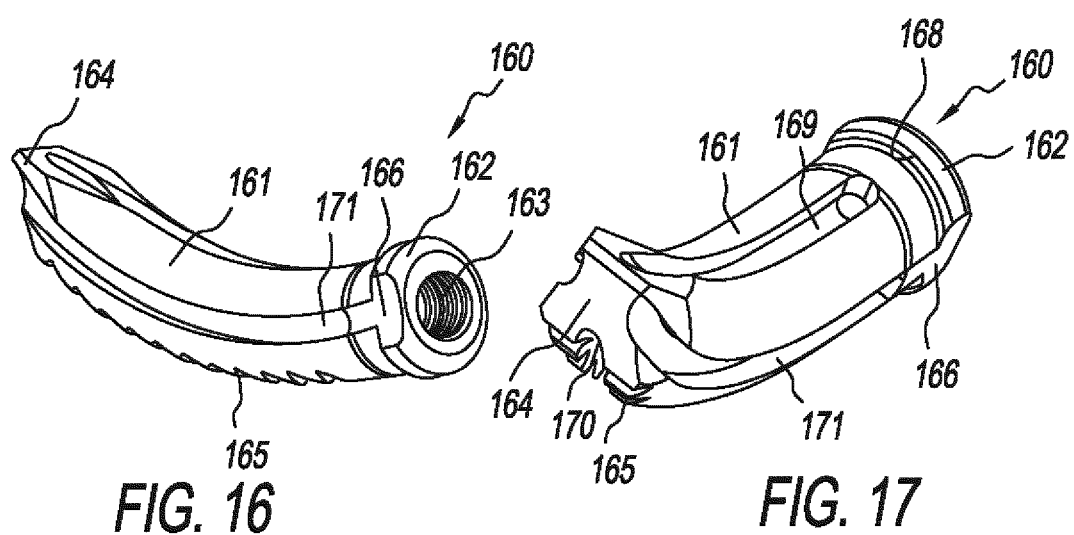
FIG. 16
FIG. 17

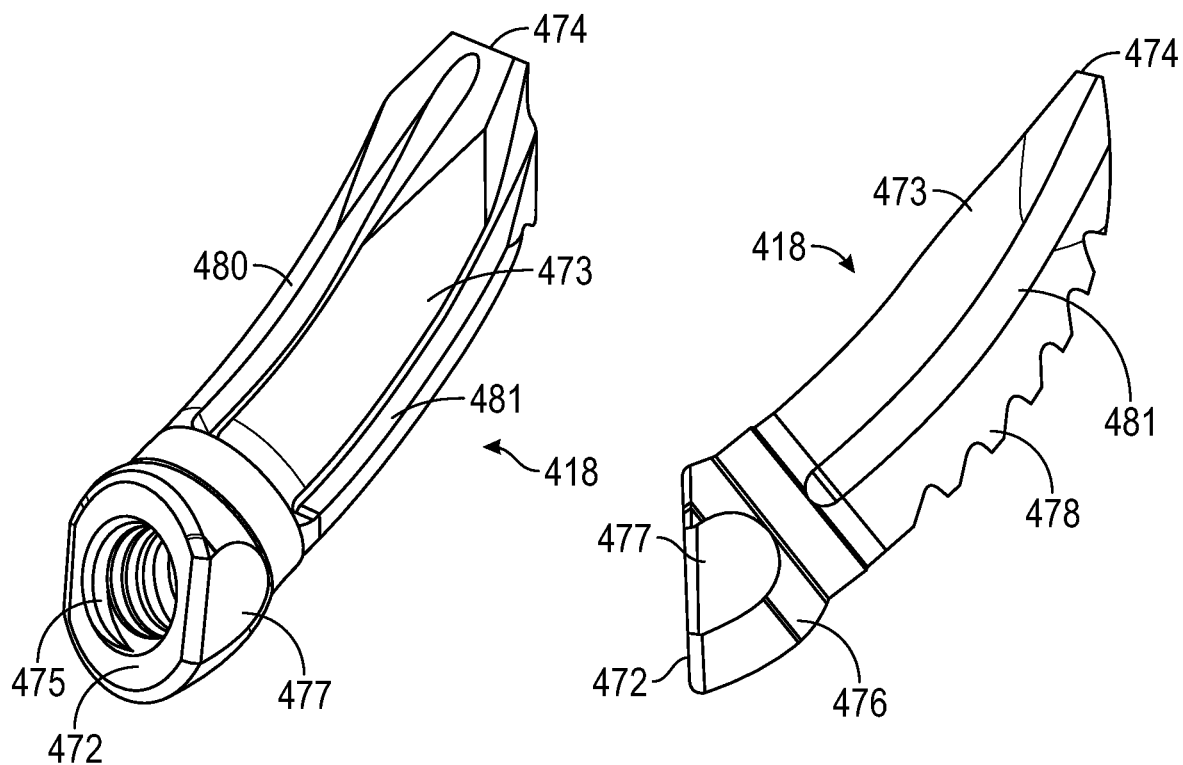
FIG. 45  FIG. 46
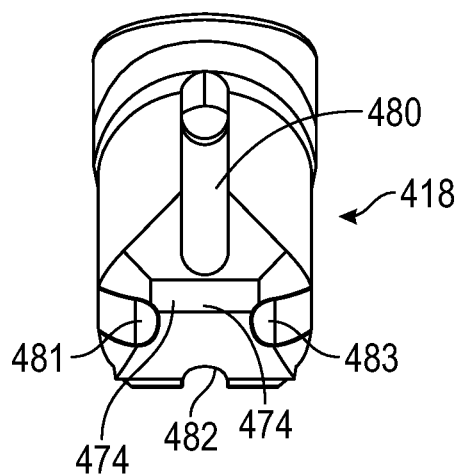
FIG. 47

IMPLANT WITH BONE SCREW RETENTION

CROSS-REFERENCE TO RELATED APPLICATIONS

This application is a continuation of U.S. application Ser. No. 16/734,232, filed Jan. 3, 2020, which is a continuation-in-part of U.S. application Ser. No. 15/957,021, filed Apr. 19, 2018, which claims priority to and the benefit of U.S. Provisional Application No. 62/487,092 filed Apr. 19, 2017, all of which are incorporated herein by reference in their entireties.

BACKGROUND

The present disclosure generally relates to methods and devices for orthopedic surgery. More specifically, the present disclosure relates to the present disclosure relates to methods and devices for orthopedic surgery of the spine and, particularly, to methods and devices for anterior lumbar interbody fusion (ALIF). Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

A fusion of the lumbar region of the spine (a lumbar fusion) may be accomplished using several techniques. Once such technique is known as an anterior lumbar interbody fusion or ALIF. ALIF spine surgery is performed through the anterior aspect of the spine and provides stabilization of the spine. In an ALIF, the disc space is fused by approaching the spine through the abdomen. In one approach, an incision is made on the left side of the abdomen and the abdominal muscles are retracted to the side. Since the anterior abdominal muscle in the midline (the rectus abdominis) runs vertically, it does not need to be cut and easily retracts to the side. The abdominal contents lay inside a large sack (peritoneum) that can also be retracted, thus allowing the spine surgeon access to the front of the spine without actually entering the abdomen.

After the blood vessels have been moved aside, the disc material is removed and bone graft typically with an anterior interbody cage is inserted. The ALIF approach leaves both the back muscles and nerves remain undisturbed. Additionally, placing the bone graft in the front of the spine places it in compression, and bone compression tends to fuse better. Moreover, a much larger implant can be inserted through an anterior approach, providing for better initial stability of the fusion construct. When an interbody cage is used, it is important that it is securely anchored.

However, there is room for improvement over current ALIF implants, instruments, and/or surgical procedures.

In view of the above, it is an object of the present disclosure to provide an improved ALIF implant, an instrument for implanting the improved ALIF, and/or a surgical procedure for the implantation.

SUMMARY

ALIF spine implants (ALIF implants), ALIF installation instruments/tools, and ALIF procedures using the ALIF implants and ALIF installation instruments for an anterior lumbar interbody fusion (ALIF) surgical procedure are provided. The ALIF implants are characterized by an ALIF cage and anchoring members. The ALIF installation instruments are characterized by a shaft having an inserter on one end that receives and holds an ALIF cage and anchoring members. The installation instrument allows insertion of the ALIF cage into a vertebral space, the anchoring members to be received in the ALIF cage, and then into vertebral bone.

Each ALIF cage is characterized by a porous body that may be, but not necessarily, 3-D printed, having a central cavity, an end configured to accept a plurality of anchoring members and direct a portion of the anchoring members up and out of the cavity, a cutout configured to receive an anchoring member retention component, and an anchoring member retention component.

The anchoring member retention component may be a set screw or plate. The plate may be a separate piece or may be pivotally attached to the ALIF cage via a hinge or other pivot structure.

The anchoring members may be curved anchoring barbs or linear anchoring screws.

Upper (superior) surfaces of the body of the ALIF implant and lower (inferior) surfaces of the body of the ALIF implant may, but not necessarily, each have serrations, teeth or the like.

A form of the ALIF instrument is characterized by a hollow shaft extending from a handle, the hollow shaft having a distal end that is attached to an inserter. The inserter is configured to receive and hold the ALIF cage, and to receive and direct anchoring members into the ALIF cage. As such, the inserter has curved channels, one curved channel for each anchoring member along with a leaf spring that retains the anchoring member within its curved channel. An impactor is used to urge or push the anchoring members from the inserter into the ALIF cage, then into the vertebral bone.

In the case of the ALIF cage having a pivoting anchoring member retention component, the inserter has a lateral channel that receives the pivoted anchoring member retention component. Once the ALIF cage is disengaged from the inserter, the anchoring member retention component is pivoted to cover the inserted anchoring members. This inhibits, if not prevents, anchoring member back-out.

In further embodiments, an implant is disclosed. The implant includes a plurality of anchoring members and an interbody device having a front, a rear, a first lateral side, a second lateral side, a central cavity, and a plurality of bores each configured to receive one of the plurality of anchoring members. The interbody device includes a porous portion and a solid portion. The solid portion has a higher density than the porous portion. The solid portion substantially surrounds the porous portion on the lateral outer portions of the front, rear, first lateral side, and second lateral side.

In further embodiments, an implant is disclosed. The implant includes a plurality of anchoring members and an interbody device having a front, a rear, a first lateral side, a second lateral side, a central cavity, and a plurality of bores each configured to receive one of the plurality of anchoring members. The interbody device includes a porous portion and a solid portion, the solid portion having a higher density than the porous portion. The first lateral side includes a first lateral window extending through the solid portion and the second lateral side includes a second lateral window extending through the solid portion.

In further embodiments, an implant is disclosed. The implant includes an anchor member and an implant body comprising an inner lateral peripheral portion comprising a porous material and defining a central cavity, an outer lateral peripheral portion comprising a solid material and surrounding the inner lateral peripheral portion, and at least one bore configured to receive the anchor member to secure the implant to adjacent bone. The implant body is formed as a single integral piece.

In further embodiments, an implant is disclosed. The implant includes an anchoring member and an implant body. The implant body includes at least one bore configured to receive the anchor member to secure the implant to an adjacent bone. The implant further includes an installation tool interface, and an installation tool. The installation tool includes an interface body configured receive the implant body, wherein the interface body can controllably attach the implant body to the installation tool, a retention member configured to selectively release the implant body, and a drive member configured to drive the anchoring member into the adjacent bone while the installation tool is attached to the implant body.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

The features of the subject matter disclosed herein will be better understood by reference to the accompanying drawings which illustrate the subject matter disclosed herein, wherein:

FIG. 15 is an isometric view of the ALIF implant of FIG. 14 with its hinged cover plate in an open position with two anchoring barbs fully inserted and one anchoring barb ready to be inserted therein;

FIG. 16 is an isometric view of the anchoring barb of the ALIF implant of FIG. 10;

FIG. 17 is an isometric view of the anchoring barb of FIG. 16;

FIG. 45 is a perspective view of a bone barb according to an example embodiment.

FIG. 46 is a side view of the bone barb of FIG. 45 according to an example embodiment.

FIG. 47 is a front view of the bone barb of FIG. 45 according to an example embodiment.

Figure 1:
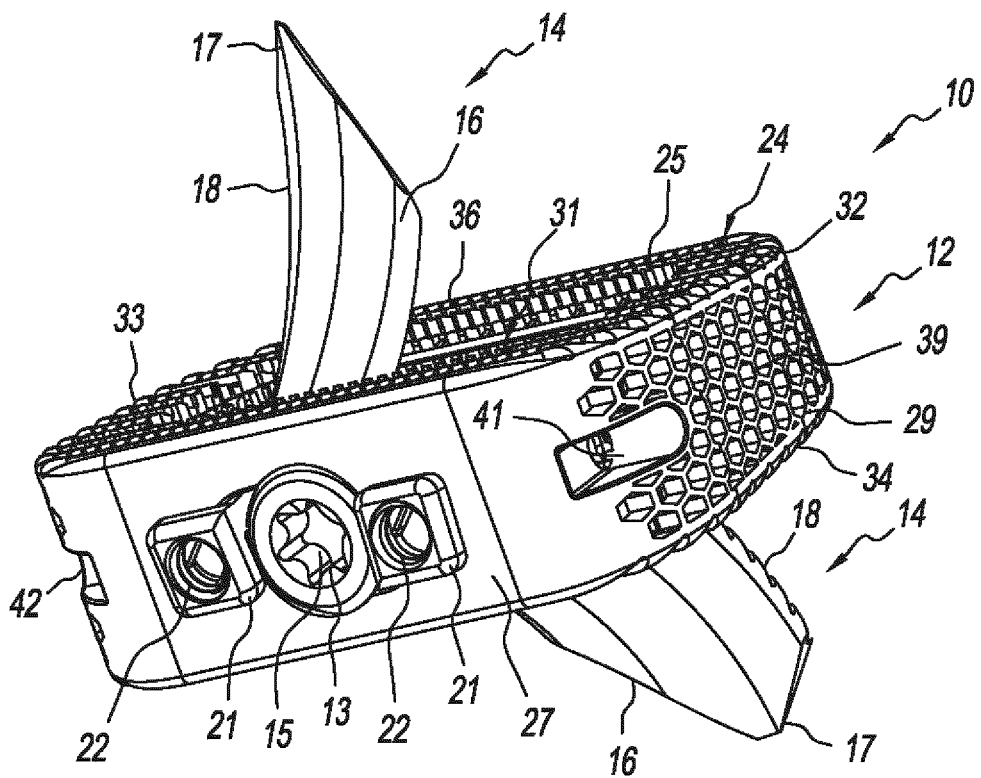
FIG. 1 is an isometric view of an ALIF implant fashioned in accordance with the present principles with anchoring barbs fully installed therein.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring to FIGS. 1-9, there is depicted a form of an anterior lumbar interbody fusion (ALIF) implant (ALIF spine implant or ALIF implant), generally designated 10, fashioned in accordance with the present principles. The ALIF implant 10 is made from a biocompatible material such as, but not limited to, PEEK, PETE, other plastic or polymer, titanium, stainless steel, an alloy of titanium or stainless steel, or otherwise. The ALIF implant may, but not necessarily, be 3-D printed. The ALIF spine implant (spine implant) 10 has a porous cage or interbody device 12, two or more anchoring members 14, each anchoring member 14 fashioned as a barb, blade, shim or the like (herein "barb") 14, and a set screw (anchoring member) 13.

Figure 2:
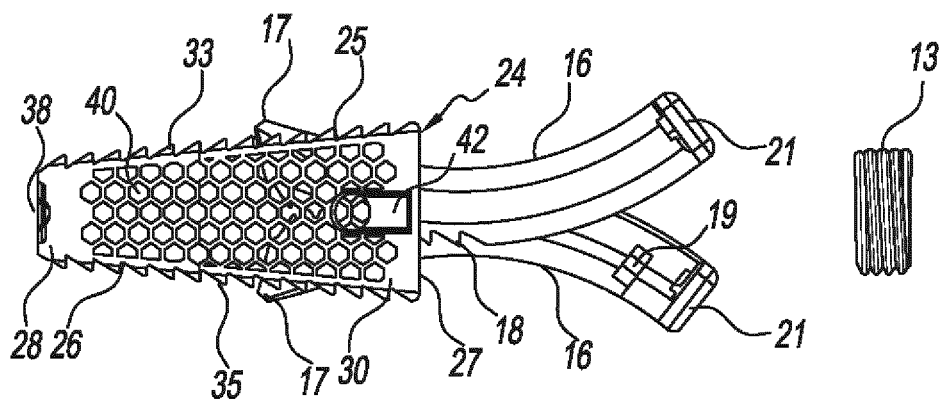
FIG. 2 is a side view of the ALIF implant of FIG. 1 showing the anchoring barbs being inserted into the ALIF cage with a set screw of the ALIF implant shown exploded relative to the ALIF cage.
Figure 3:
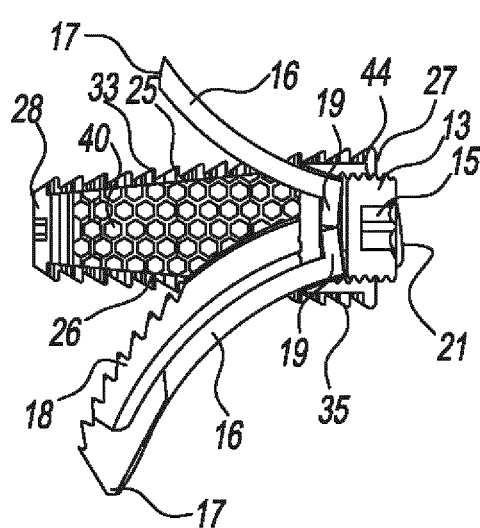
FIG. 3 is a side sectional view of the ALIF implant of FIG. 1 showing the anchoring barbs fully inserted into the ALIF cage but before being compressed by the set screw.
Figure 4:
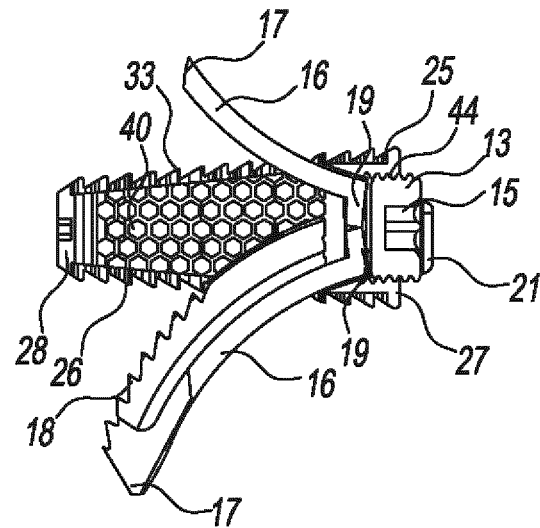
FIG. 4 is a side sectional view of the ALIF implant of FIG. 1 showing the barbs fully inserted into the ALIF cage and fully compressed by the set screw.

The set screw 13 is generally cylindrical with external threads. A socket 15 is provided in the top of the set screw 13 that is configured to receive a tool (not shown) for installing the set screw into the porous cage 12. As seen in FIGS. 2-4, the set screw 13 is used to keep the barbs 14 from backing out of the porous cage 12 as well as to compress the operative level after the barbs 14 are impacted into vertebral bone by forcing the barbs 14 to pivot toward each other, resulting in segmental compression. FIG. 2 shows the barbs 14 being received into the porous cage 12 with the set screw 13 ready for insertion. FIG. 3 shows the barbs 14 fully inserted into the porous cage 12 with the set screw 13 also received in the porous cage 12, but before compression of the barbs 14. When the set screw 13 is fully seated into the porous cage 12 (FIG. 4), the set screw 13 bottoms out against the shoulders 29 of the barbs 14 to compress against and pivot the barbs 14. FIG. 1 shows the barbs 14 fully received and compressed into the porous cage 12 by the set screw 13.

Figures 7, 8:
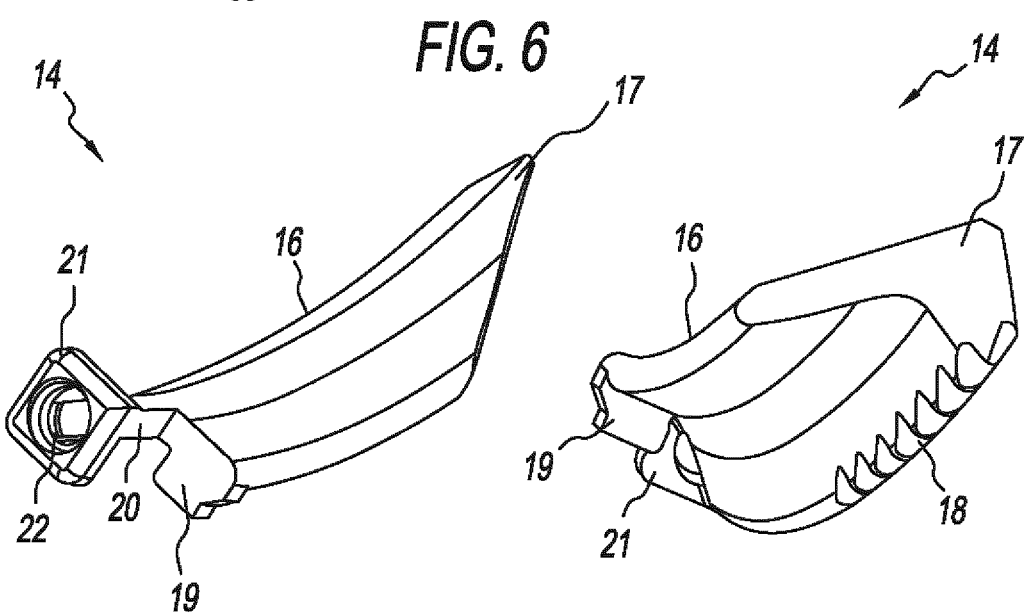
FIG. 7 is an isometric view of the anchoring barb of the ALIF implant of FIG. 1.
FIG. 8 is an enlarged view of a portion of the anchoring barb of FIG. 7.
Figure 9:
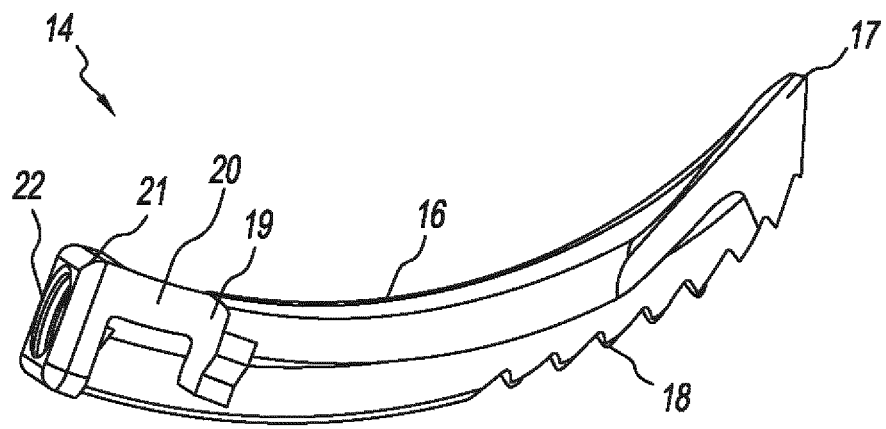
FIG. 9 is a side view of the anchoring barb of FIG. 7.
Figure 10:
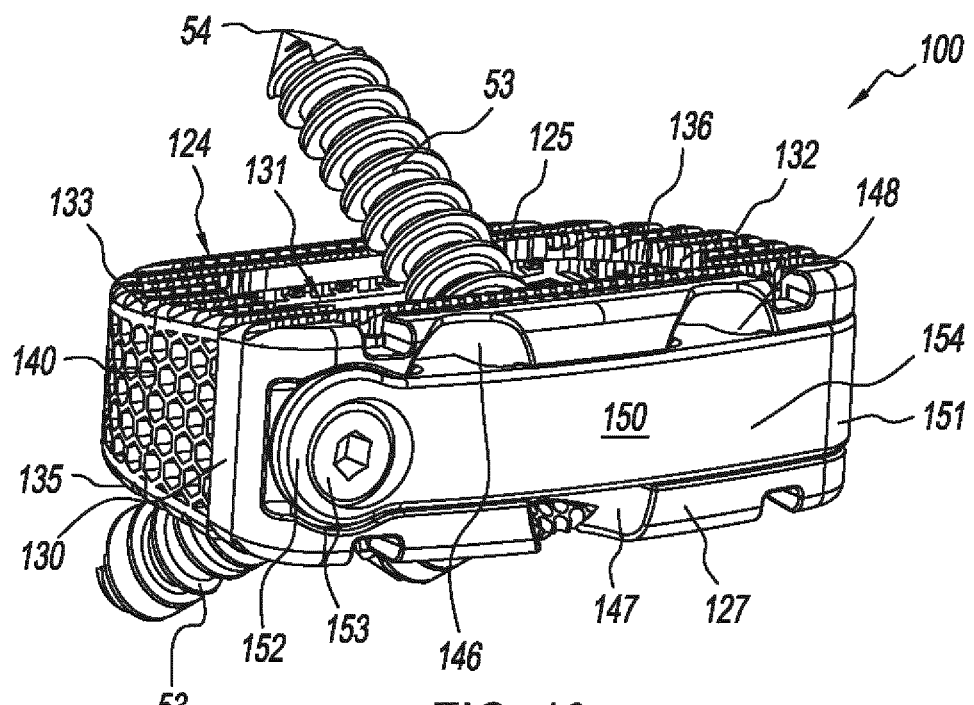
FIG. 10 is an isometric view of another ALIF implant fashioned in accordance with the present principles with all anchoring screws fully installed therein.
Figure 11:
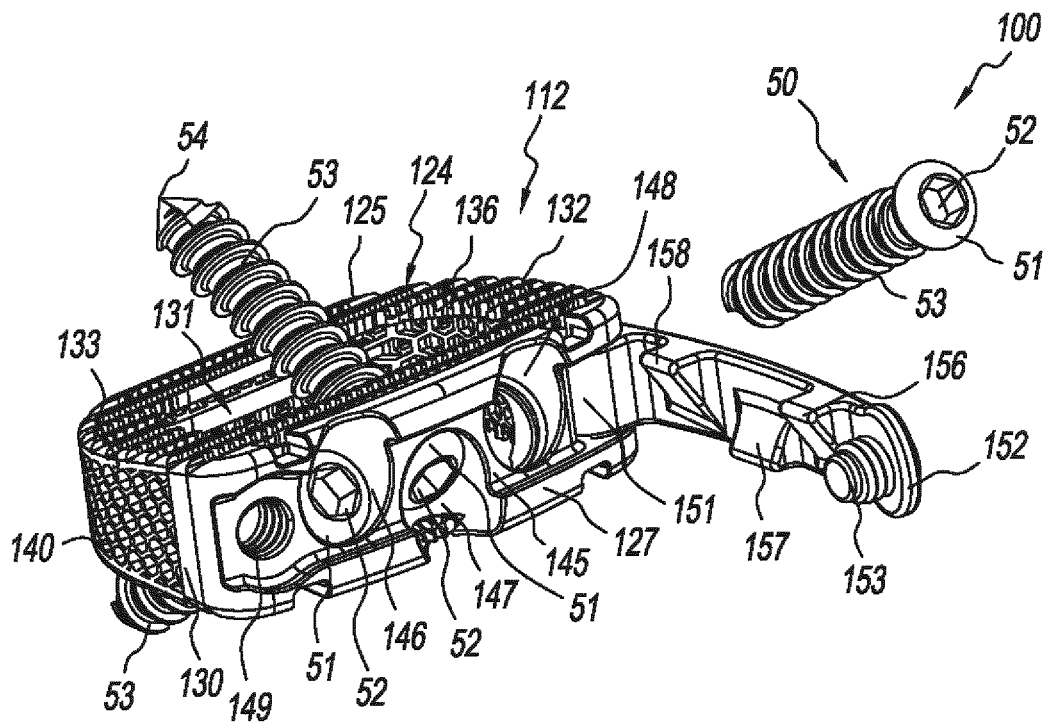
FIG. 11 is an isometric view of the ALIF implant of FIG. 10 with its hinged cover plate in an open position with two anchoring screws installed therein with one anchoring screw ready to be inserted therein.
Figure 12:
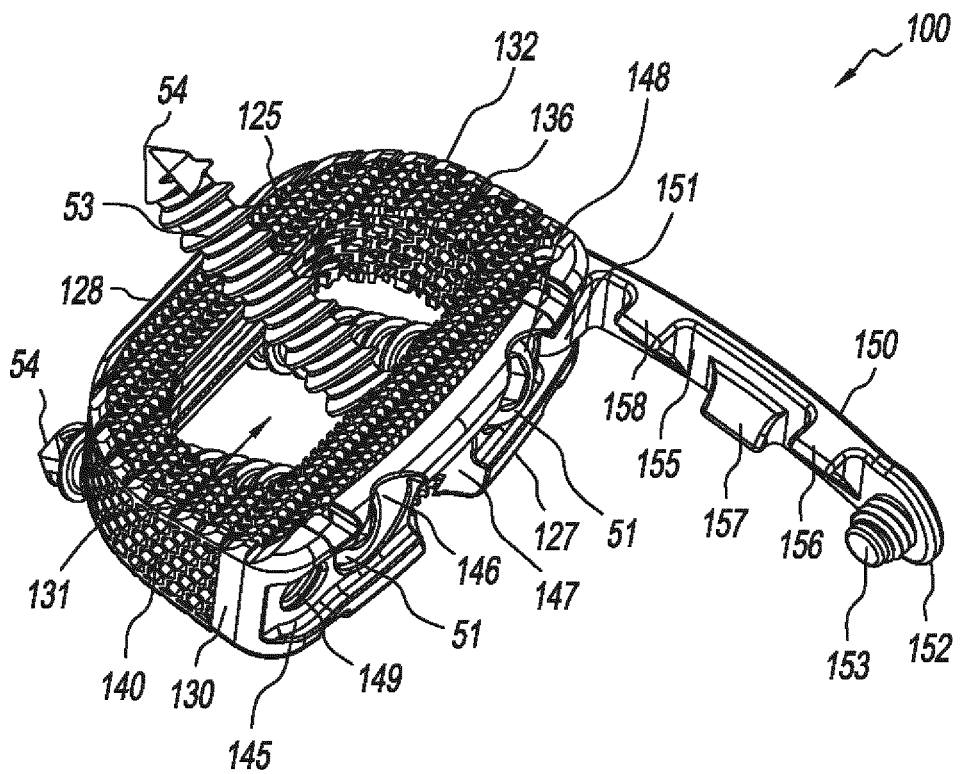
FIG. 12 is an isometric view of the ALIF implant of FIG. 10 with its hinged cover plate in an open position with all anchoring screws inserted therein.

The barb 14 is particularly shown in FIGS. 7-9 and is characterized by a curved body 16 having a head 21 at a first end, and a tip 17 at a second end, the nomenclature first and second being arbitrary. The tip 17 is generally "shovel-shaped" to provide easy piercing and/or penetration into vertebral bone. Other configurations may be used. The body 16 has an angled cross-section to increase stiffness and resistance to flexion-extension movement of the spine when implanted. The head 21 is at the end of a neck 20 that extends from one side of the curved body 16, and include a threaded bore 22. The threaded bore 22 allows for use of an extractor instrument (not shown) to withdraw the barb from the porous cage 12 if needed. The barb further includes a shoulder 19 at the first end that is axially offset from the head 21. As explained further below, when the barbs 14 are received in the porous cage 12, the set screw 13 bottoms out against the shoulders 19.

Figure 5:
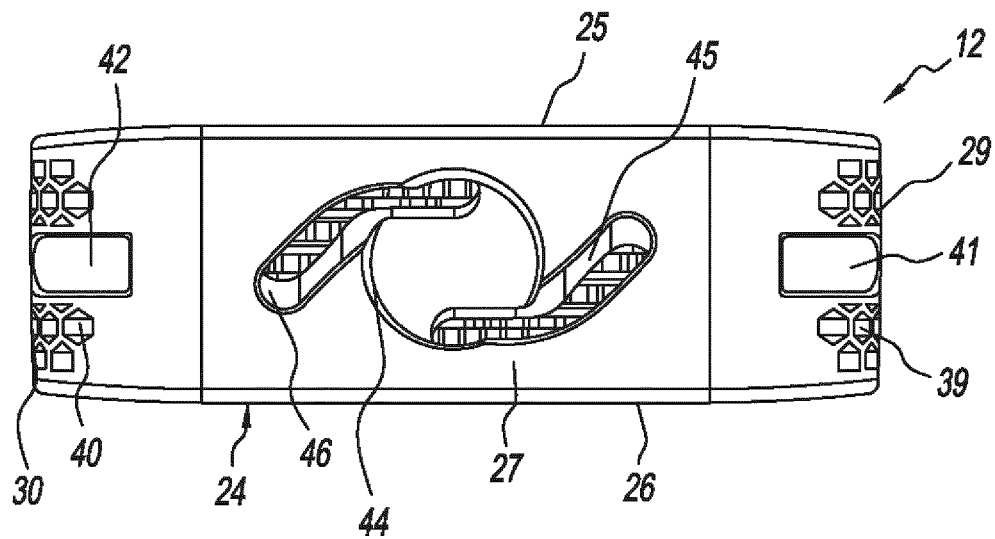
FIG. 5 is a front plan view of the ALIF cage of the ALIF implant of FIG. 1.
Figure 6:
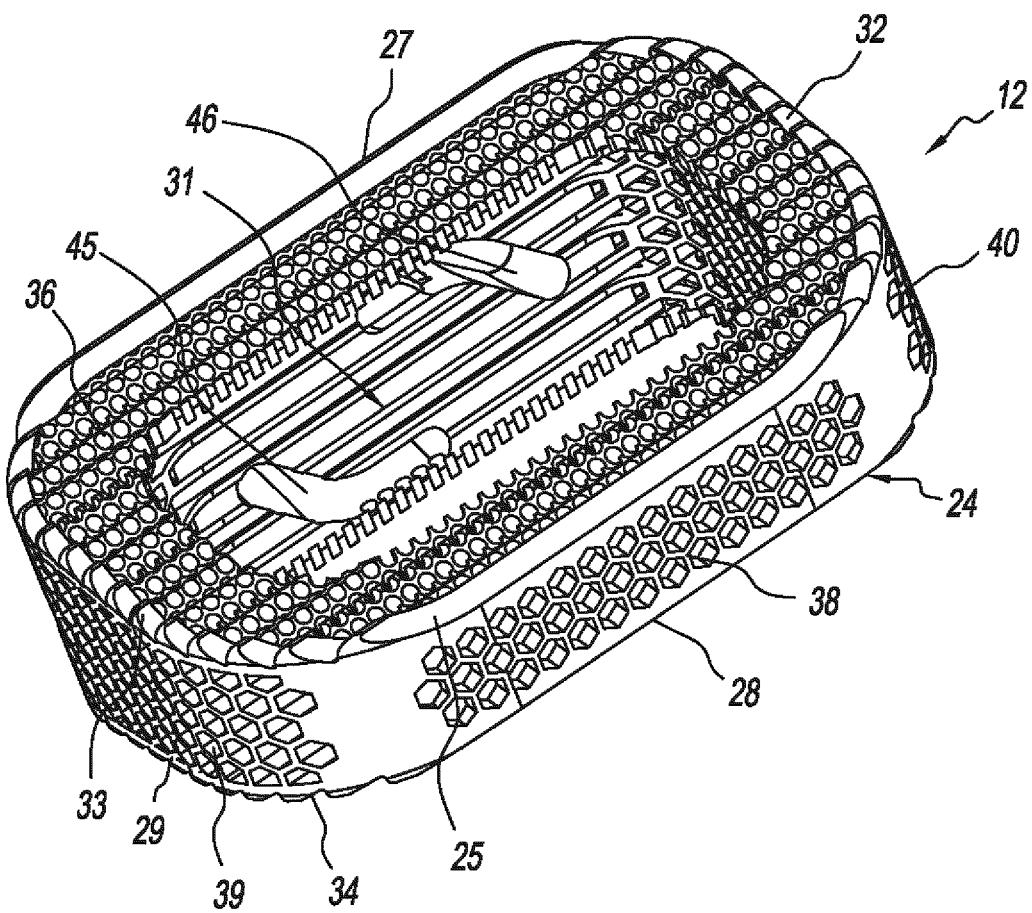
FIG. 6 is an isometric view of the ALIF cage of the ALIF implant of FIG. 1.

As most particularly seen in FIGS. 1, 5 and 6, the ALIF implant 10 is characterized by a generally porous body 24 fashioned generally as a rectangular wedge having an upper (superior) surface 25, a lower (inferior) surface 26 opposite to the upper surface 25, a first lateral side 29, a second lateral side 30 that is opposite to and identical with the first lateral side 29, a first end or front 27, and a second end or rear 28 opposite to the front 27, the nomenclature "first," "second," "front," and "rear" being arbitrary. The body 24 also has a cavity 31 that extends from the upper surface 25 to the lower surface 26. The cavity 31 is adapted or configured to receive bone graft/bone graft material such as is known in the art.

Extending along the upper surface 25 adjacent the first lateral side 29 (edge) is a section of serrations, teeth, or the like (collectively, serrations) 32, while extending along the upper surface 25 adjacent the second lateral side 30 (edge) is a second section of serrations, teeth, or the like (collectively, serrations) 33, the nomenclature "first" and "second" being arbitrary. The serrations 32, 33 provide gripping of the cage 12 to a superior vertebra/vertebral bone when implanted. In like manner, extending along the lower surface 26 adjacent the first lateral side 29 (edge) is a third section of serrations, teeth, or the like (collectively, serrations) 33, while extending along the lower surface 26 adjacent the second lateral side 30 is a fourth section of serrations, teeth, or the like (collectively, serrations) 35, the nomenclature "third" and "fourth" being arbitrary. The serrations 33, 35 provide gripping of the superior end of an inferior vertebra/vertebral bone when implanted.

The rear 28 of the body 24 defines a nose or arch having a downwardly angled or sloped upper (superior) surface, an upwardly angled or sloped lower (inferior) surface opposite to the downwardly angled upper surface, a first rounded side, and a second rounded side opposite to the first rounded side, the nomenclature "first" and "second" being arbitrary. The front 27 of the body 24 is generally planar with a large threaded bore 44 that extends therein a distance or to the cavity 31. The threaded bore 44 receives the set screw 13. A first elongated slot 41 runs from the front 27 around to and along a portion of the first lateral side 29, while a second elongated slot 42 runs from the front 27 around to and along the second lateral side 30, the nomenclature "first" and "second" being arbitrary. The first elongated slot 41 is adapted/configured to receive a first prong of an installation tool (not seen), while the second elongated slot 42 is adapted/configured to receive a second prong of the installation tool (not seen) opposite the first prong, the nomenclature "first" and "second' being arbitrary.

The front 27 also has a first curved slot 45 extending from one side of the threaded bore 44 and a second curved slot 46 extending from another side of the threaded bore 44, the curved slots 45, 46 opposite one another. The first curved slot 45 has a curvature that matches the profile of the barb 14 and which is angled such that the tip 17 and a portion of the first end thereof extends downwardly out of the cavity 31 of the body 24 of the porous cage 12 when the barb 14 is fully inserted therein. The second curved slot 46 has a curvature that matches the profile of the barb 14 and which is angled such that the tip 17 and a portion of the first end thereof extends upwardly out of the cavity 31 of the body 24 of the porous cage 12 when the barb 14 is fully inserted therein.

Referring to FIGS. 10-13, there is depicted another form of an anterior lumbar interbody fusion (ALIF) implant (ALIF spine implant or ALIF implant), generally designated 100, fashioned in accordance with the present principles. The ALIF implant 100 is made from a biocompatible material such as, but not limited to, PEEK, PETE, other plastic or polymer, titanium, stainless steel, an alloy of titanium or stainless steel, or otherwise. The ALIF implant may be 3-D printed. The ALIF spine implant (spine implant) 100 has a porous cage or interbody device 112, and three anchoring members 50, each anchoring member 50 fashioned as a screw.

The screw 50 is characterized by a linear, externally threaded shaft 53. In one embodiment, the externally threaded shaft 53 has a constant diameter, while in other embodiments, the externally threaded shaft 53 has a variable diameter. The screw 50 has a head 52 at a first end, and a tip 54 at a second end, the nomenclature first and second being arbitrary. In one embodiment, the tip 54 is pointed. The head 51 further includes a socket 52 in its upper surface that is configured to receive an installation tool (not shown).

The porous cage 112 of the spine implant 100 has the same configuration as the spine implant 10 except for its front, which is explained below. The numbering of features, components and the like of the porous cage 112 adds a "100" to the numbering of those features components and the like of the porous cage 112 that are the same as the features, components and the like of the porous cage 12. As such, the description of these features, components and the like of the porous cage 112 will not be discussed, as they have been discussed above regarding the porous cage 12.

The front 127 of the porous cage 112 includes a channel 145 that extends generally from the second lateral side 140 to the first lateral side 139. A first angled screw bore 146 is provided in the front 127 of the body 124 proximate the second lateral side 140. The bore 146 extends from the front 127 to the cavity 131 and is sized to allow the threaded shaft 53 of the screw 50 to extend therethrough and into the cavity 131, the front of the bore 146 defining a pocket sized to capture the screw head 51. The bore 146 is angled downwardly such that the threaded shaft 53 and thus the tip 54 of the screw 50 extends downwardly out of the cavity 131. A second angled screw bore 147 is provided in the front 127 of the body 124 proximate a middle of the front 127. The bore 147 extends from the front 127 to the cavity 131 and is sized to allow the threaded shaft 53 of the screw 50 to extend therethrough and into the cavity 131, the front of the bore 147 defining a pocket sized to capture the screw head 51. The bore 147 is angled upwardly such that the threaded shaft 53 and thus the tip 54 of the screw 50 extends upwardly out of the cavity 131. A third angled screw bore 148 is provided in the front 127 of the body 124 proximate the first lateral side 139. The bore 148 extends from the front 127 to the cavity 131 and is sized to allow the threaded shaft 53 of the screw 50 to extend therethrough and into the cavity 131, the front of the bore 148 defining a pocket sized to capture the screw head 51. The bore 148 is angled downwardly such that the threaded shaft 53 and thus the tip 54 of the screw 50 extends downwardly out of the cavity 131. It should be appreciated that the angle of the bores may be changed as desired. The front 127 also includes a threaded hole 149 in the channel 145 adjacent the second lateral side 140. The threaded hole 149 is sized to accept a machine screw 153 of an anchoring member retention component 150.

The anchoring member retention component 150 is in the form of a plate that is pivotally connected to the front 127 of the porous cage 112 via a hinge 151, the hinge 151 is situated adjacent the first lateral side 139. The hinge 151 includes a pivot pin that is received in the body 124 and through the end of the plate 150. In one embodiment, the plate 150 is sized for reception in the channel 145 of the front 127 with a friction fit to prevent "flopping." The plate (lid, or latch) 150 may prevent back-out of the bone screws 50. In one embodiment the plate 150 prevents back-out by making contact with the head of the bone screw 50 once the plate 150 is secured to the cage 112. The plate 150 has a boss 152 on its end opposite the hinge 151 that permanently holds the machine screw 153 but allows its rotation. The machine screw 153 is receivable in the threaded bore 149 in order to secure the plate 150 to the body 124. The plate 150 has a generally smooth outer surface 154.

In order to aid in anchoring member back-out prevention, an inside surface 155 of the plate has three (3) protrusions or projections 156, 157, 158 corresponding in number to and position of the angled bores 146, 147, 148 of the front 127. Each projection 156, 157, 158 is generally triangular shaped in order to fit into the pocket formed by the bore 156, 157, 158. Once the plate 150 is closed, the projection 156 of the plate 150 is received in the bore pocket 146, the projection 157 of the plate 150 is received in the bore pocket 147, and the projection 158 of the plate is received in the bore pocket 148.

Figure 13:
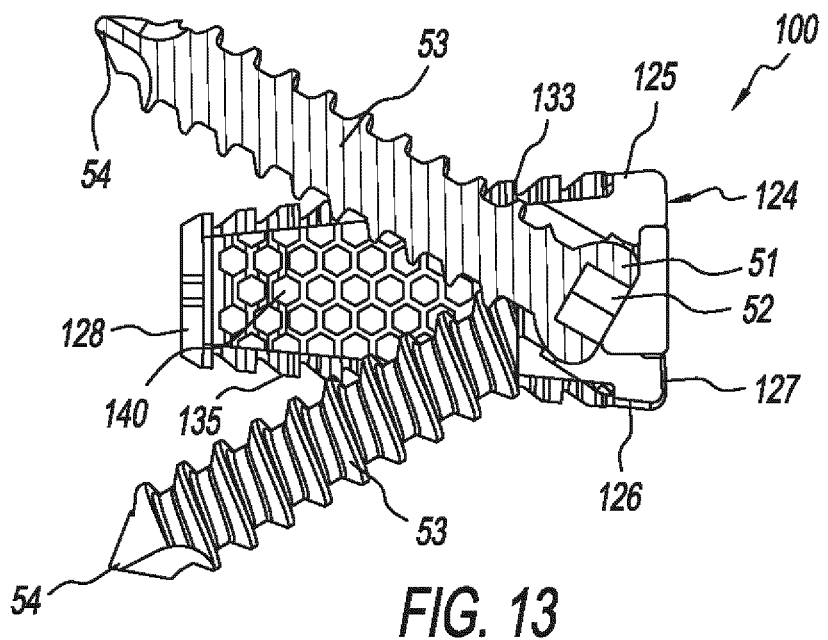
FIG. 13 is a side sectional view of the ALIF implant of FIG. 10 with all anchoring screws fully inserted into the ALIF cage.
Figure 14:
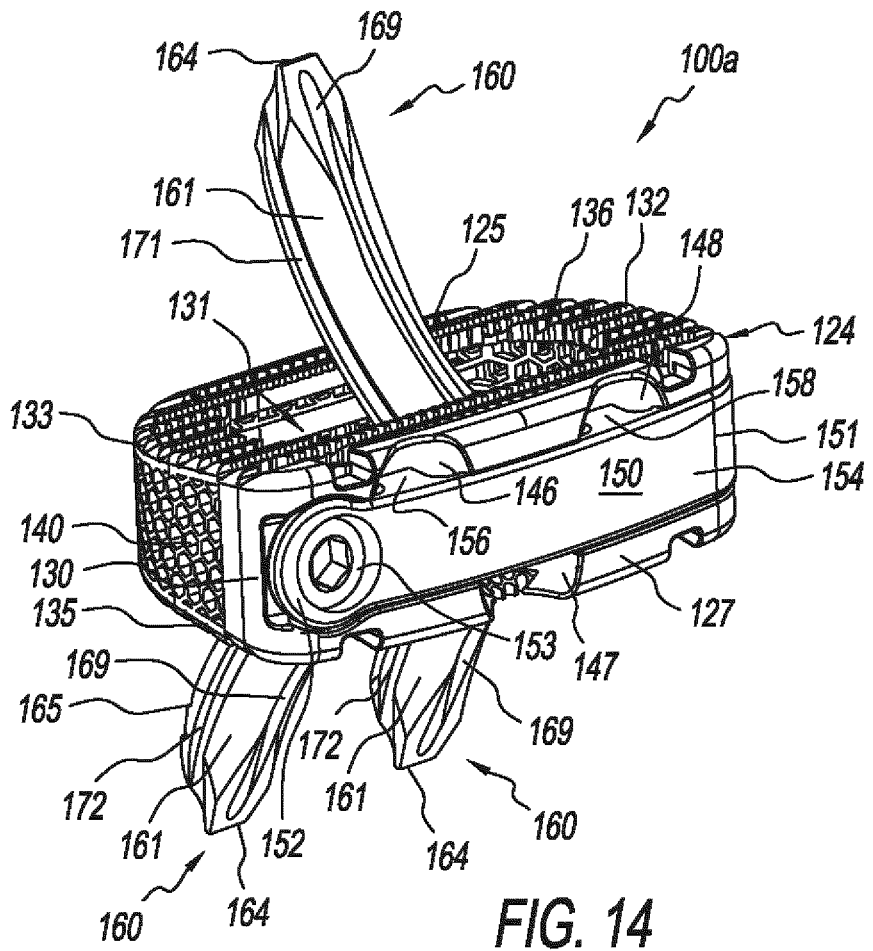
FIG. 14 is an isometric view of another ALIF implant fashioned in accordance with the present principles with anchoring barbs fully installed therein.
Figure 18:
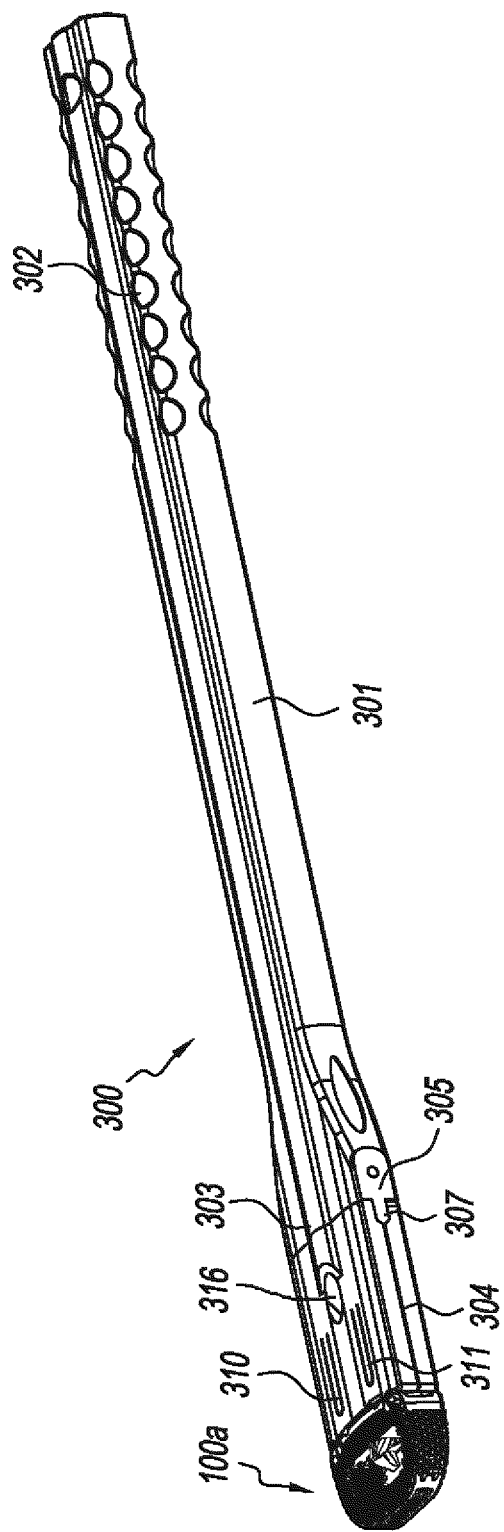
FIG. 18 is an isometric view of an installation tool for the ALIF implant of FIGS. 10-17.
Figure 19:
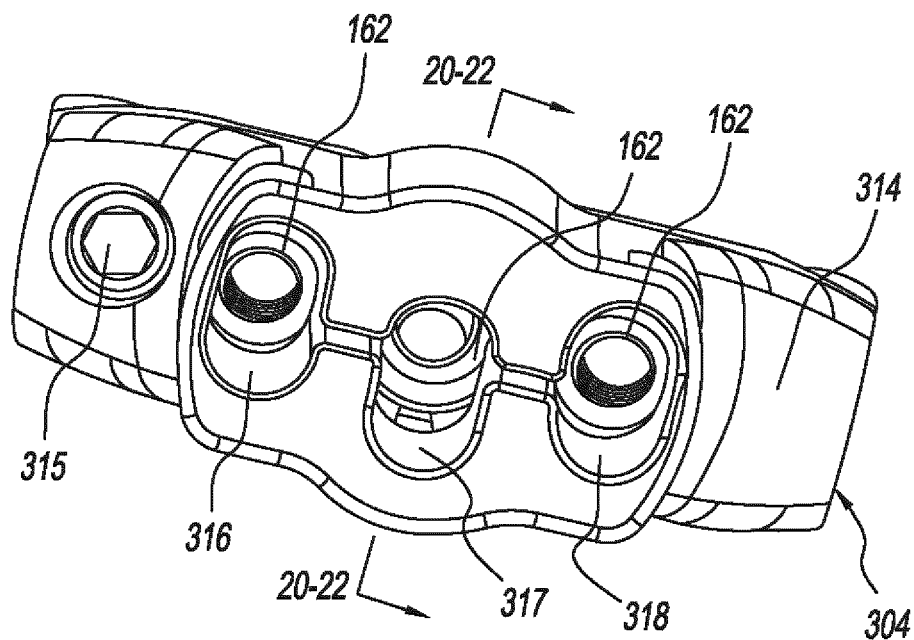
FIG. 19 is an isometric view of a front of an inserter portion of the installation tool of FIG. 18.

Referring to FIG. 13, the exit diameter of the openings in the cage can either allow or disallow bone screws to angulate in the sagittal plane. Variable angle fasteners are shown. Moreover, the protrusions 156, 157, 158 of the plate 150 make contact with the heads of the bone screws 50 once the latch is secure. The protrusions 156, 157, 158 of the plate 150 may also be configured to generate segmental compression by forcing anchoring members (bone screws) to pivot toward the coronal mid-plate of the disc space when the machine screw 153 is tightened.

Referring to FIGS. 14-17 there is depicted another form of an anterior lumbar interbody fusion (ALIF) implant (ALIF spine implant or ALIF implant), generally designated 100a that is the same as the ALIF spine implant 100 except the spine implant 100a uses three (3) barbs 160 rather than three (3) bone screws 50. The porous cage 112 of the spine implant 100a has the same configuration as the spine implant 100. As such, the description of these features, components and the like of the spine implant 100 is applicable to the spine implant 100a and will not be discussed again.

As best seen in FIGS. 16-17, the barb 160 is characterized by a curved shaft 161 having a constant diameter. The barb 160 has a head 162 at a first end, and a tip 164 at a second end, the nomenclature first and second being arbitrary. The tip 164 is may be generally chisel-shaped, but other configurations may be used. The head 162 includes a socket 163 in its upper surface that is configured to receive an installation tool (not shown). The underside 168 of the head 162 defines a shoulder that bottoms out on the cage. The head 162 also has a flat 166 on one side and another flat (not seen) on the other side. Four grooves (or similar feature) 169, 170, 171, 172 are provided on the outside surface of the barb 161. In one embodiment, the grooves 169, 170, 171, 172 extend from the tip 164 to the head 162. The grooves reduce the cross-sectional area of the barbs thereby reducing the amount of material (bone) that has to be displaced in order for the barbs to be impacted into the vertebral bone.

Figure 24:
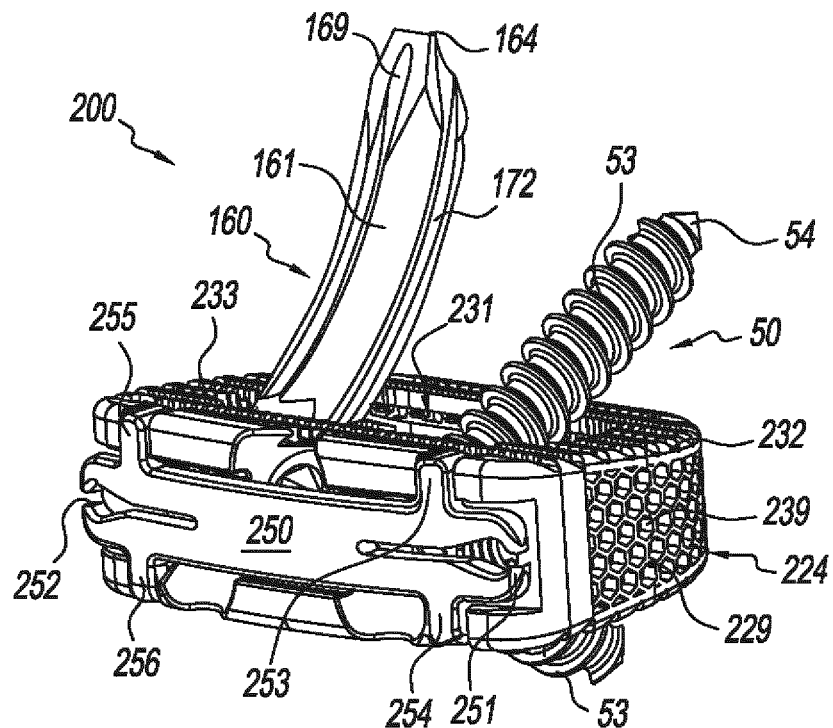
FIG. 24 is an isometric view of another ALIF implant fashioned in accordance with the present principles, the ALIF implant using anchoring barbs and anchoring screws.
Figure 25:
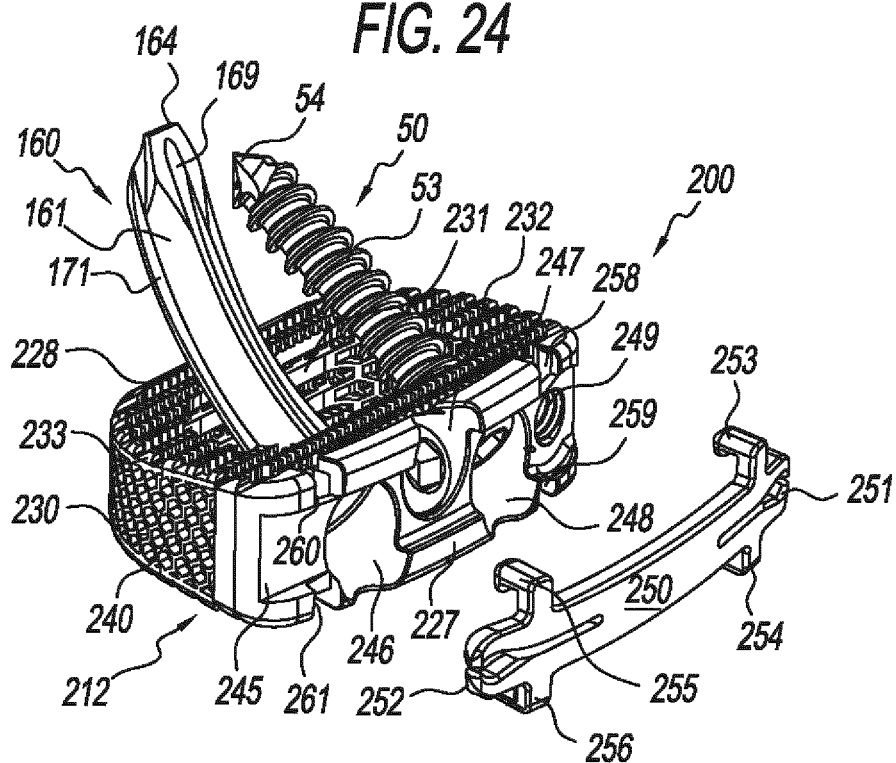
FIG. 25 is an isometric view of the ALIF implant of FIG. 24 with its cover plate removed and in an exploded view.

Referring to FIGS. 24-25 there is depicted another form of an anterior lumbar interbody fusion (ALIF) implant (ALIF spine implant or ALIF implant), generally designated 200 that is the same as the ALIF spine implants 100 and 100a except the spine implant 200 uses two (2) screws 50 and one (1) barb 160. Other combinations of screws 50 and barbs 160 can be used. The spine implant 200 has the same configuration as the spine implants 100 and 100a with the exception of the front 227 and the anchoring member retention component 250. The numbering of features, components and the like of the spine implant 200 adds a "200" to the numbering of those features components and the like thereof that are the same as the features, components and the like of the spine implants 100, 100a except as noted. As such, the description of these features, components and the like will not be discussed, as they have been discussed above.

The channel 245 of the front 227 includes an upper slot 258 and a lower slot 259 proximate the first lateral side 239, and an upper slot 260 and a lower slot 261 proximate the second lateral side. The anchoring member retention component 250 is in the form of a plate that is friction or press-fit into the front 127 of the porous cage 112. The plate 250 includes an upper hook 253 and a lower hook 254 on a first end of the plate 250 (corresponding to the first lateral side 239 of the cage 212), and an upper hook 255 and a lower hook 256 on a second end of the plate 250 (corresponding to the second lateral side 240 of the cage 212. The upper hook 253 is received in the upper slot 258, the lower hook 254 is received in the lower slot 259, the upper hook 255 is received in the upper slot 260, and the lower hook 256 is received in the lower slot 261. Moreover, the first end of the plate 250 has a resilient clip and slot structure 251, while the second end of the plate 250 has a second resilient clip and slot structure 252. The clip and slot structures 251, 252 accept mating features on a plate-inserter instrument (not shown) that, when engaged, deflects the branches of the clip and slot structures 251, 252 away from each other allowing the plate to engage the mating recesses on the front 127. When the plate inserter instrument is detached, the branches spring back toward each other. The purpose of the plate or lid 250 is to prevent back-out of the anchoring members.

Figure 20:
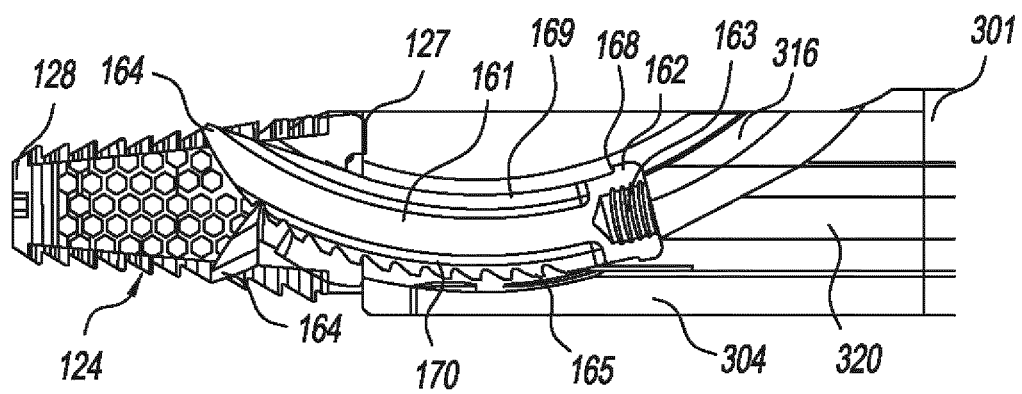
FIG. 20 is a sectional view of the inserter portion of the installation tool of FIG. 18 with an ALIF implant of FIGS. 10-17 attached thereto for implantation in the spine, this figure being a first figure of a three figure sequence illustrating insertion of an anchoring barb into the ALIF implant through the inserter portion.
Figure 21:
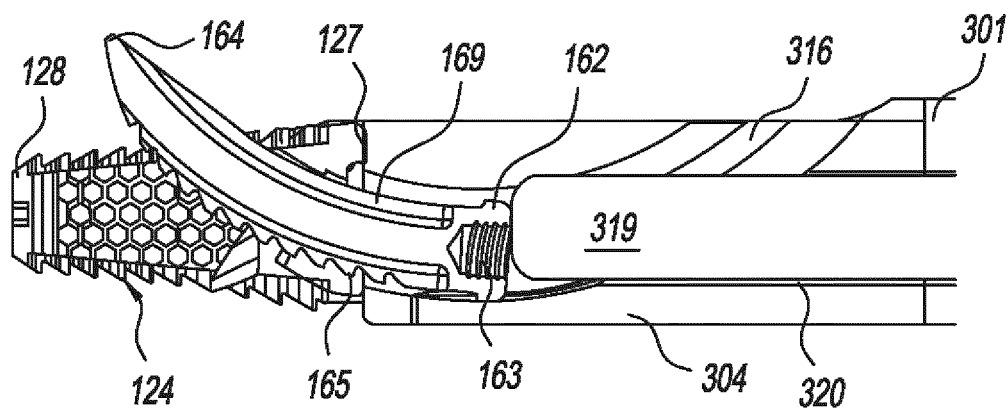
FIG. 21 is a second figure of the three figure sequence showing the sectional view of the inserter portion of the installation tool of FIG. 18 with the anchoring barb being pushed into the ALIF implant via a pusher rod of the installation tool.
Figure 22:
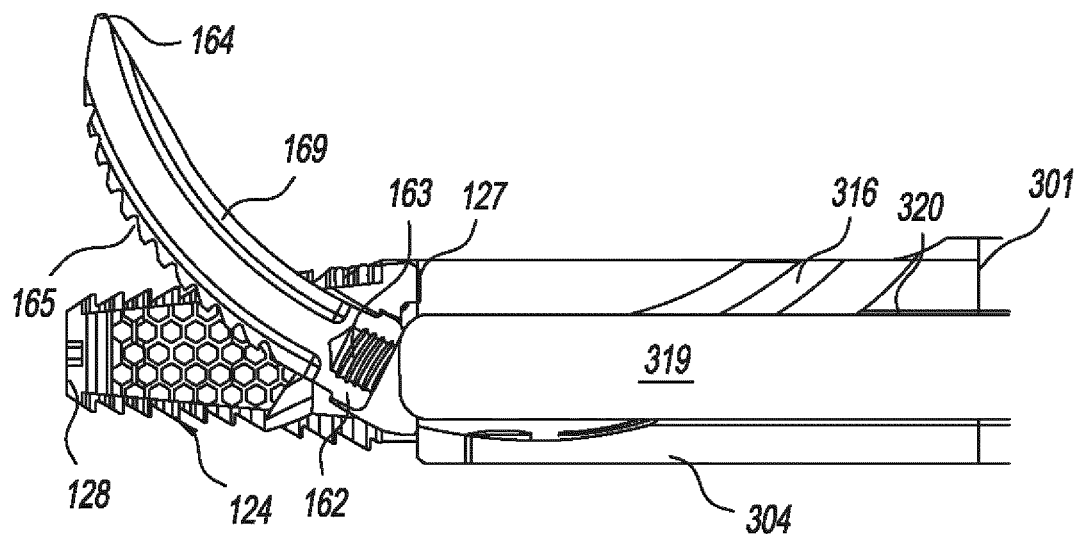
FIG. 22 is the third figure of the three figure sequence showing the sectional view of the inserter portion of the installation tool of FIG. 18 with the anchoring barb fully inserted into the ALIF implant via the pusher rod of the installation tool.
Figure 23:
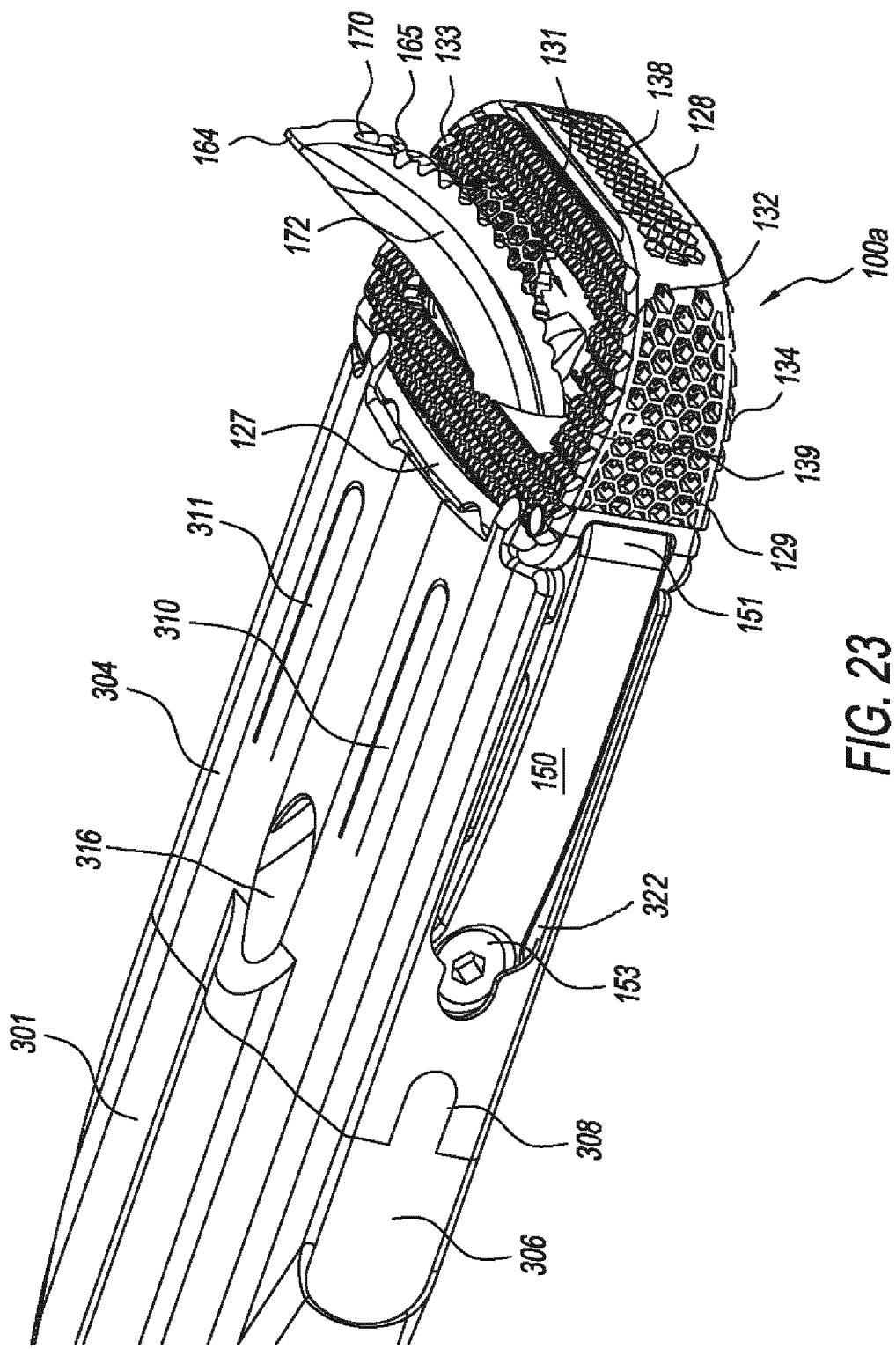
FIG. 23 is an enlarged isometric view of the inserter portion of the installation tool of FIG. 18 with all anchoring barbs fully inserted into the ALIF implant.

Referring to FIGS. 18-23, there is shown an exemplary instrument or tool 300 for installing/implanting the ALIF implants 100, 100a, and 200. The instrument 300 includes a shaft 301 with a handle 302 at one end, a neck 303 at the other end, and an inserter 304 connected to the neck 303. The neck 303 has a first prong 305 on one side, and a second prong 306 on another, opposite side. A proximal end of the inserter 304 has a first notch 307 on one side corresponding to the first prong 305 and shaped to receive same, and a second notch 308 on another, opposite side corresponding to the second prong 306 and shaped to receive same. The neck 303 and/or the shaft 301 has one or more pushers (of which a single pusher 319 is shown in FIGS. 20-22) for urging a barb 160 (anchoring member) from the inserter, into the cage body 124, then into vertebral bone (not shown). As seen in FIG. 23, a channel 322 is provided in a lateral side of the inserter 304 for receipt of the anchoring member retention component (e.g. plate 150), which holds the plate 150 in an open position during cage implantation. As seen in the example embodiment shown in FIG. 19, the inserter 304 has a threaded hole 315 that is used to attach the inserter to the cage, the shaft having a shoulder that bottoms out on inserter features once threaded onto the cage and is permanently detained within the inserter. The inserter 304 also has three (3) leaf springs 310, 311, 312 or the like corresponding in number to the number of curved channels for the anchoring members (e.g. barbs). Each leaf spring interacts with the serrations 165 of the barb 160 to retain the barb 160 through ratcheting.

The inserter 304 has three curved channels 316, 317, and 318 corresponding in number to the number of anchoring members (e.g. barbs) used by the spine implant, here being three (3). FIGS. 20-22 are a three sequence illustration of how a barb 160 is installed into the spine implant and vertebral bone. In FIG. 20, a barb 160 is received in the curved channel 316 that is arced to direct the barb 160 upwardly out of the cavity of the cage. In FIG. 21, a pusher or impactor 319 in the channel 320 of the instrument 300 begins to contact the head 162 of the barb 160 and urge the barb 160 into the cage. In FIG. 22, the pusher 319 has fully urged the barb 160 into the cage. The other barbs 160 are installed in like manner.

Figure 26:
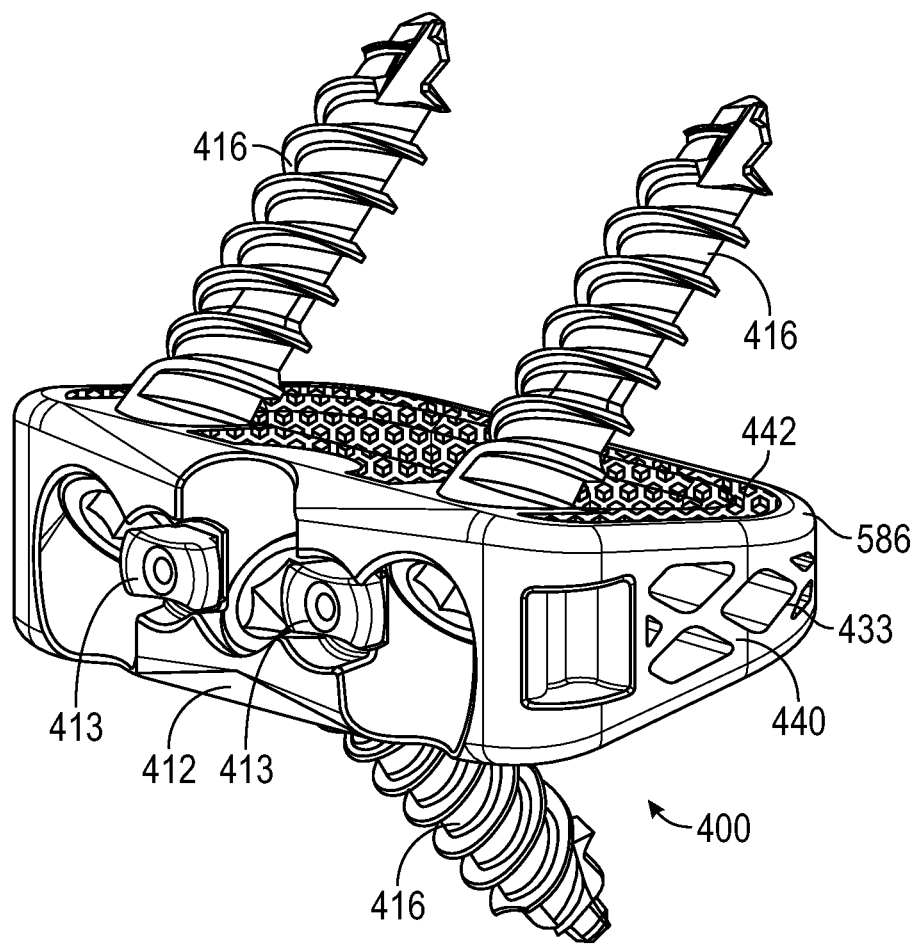
FIG. 26 is a perspective view of an implant according to another example embodiment.

Referring now to FIG. 26, an implant 400 (e.g., an anterior lumbar interbody fusion (ALIF) implant (ALIF spine implant or ALIF implant)) is shown according to one embodiment. Implant 400 is made from a biocompatible material such as, but not limited to, PEEK, PETE, other plastic or polymer, titanium, stainless steel, an alloy of titanium or stainless steel, or otherwise, or any combinations thereof. In some embodiments, the implant 400 is 3-D printed. In other example embodiments, the implant 400 may be machined, cast, or manufactured using any combination of 3-D printing, machining, casting, etc. The implant 400 includes an interbody device 412 and two or more anchoring members 414. In certain embodiments, the implant 400 also includes at least one cam screw 413.

Figure 27:
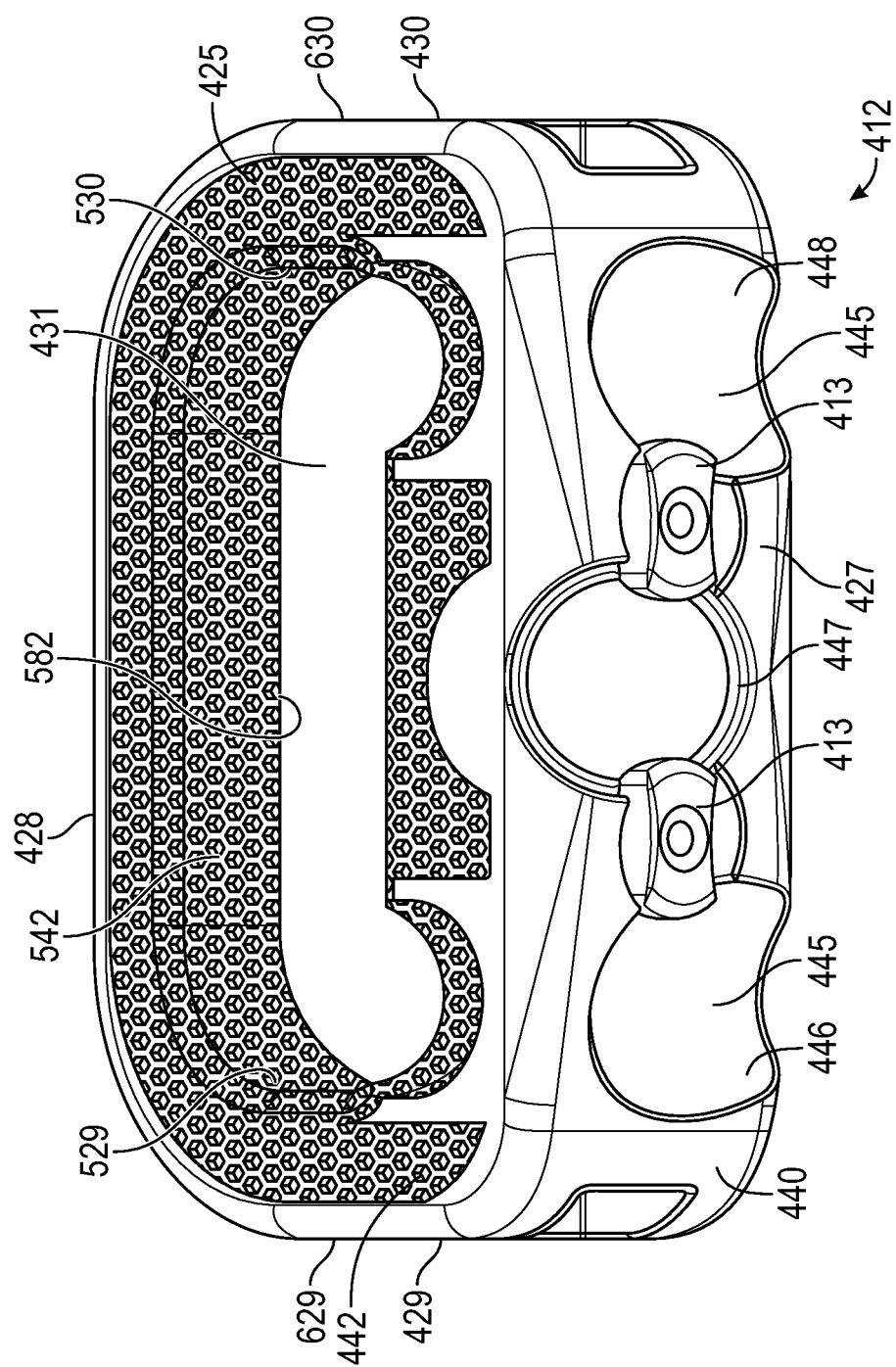
FIG. 27 is a perspective view of an interbody device of the implant of FIG. 26 according to an example embodiment.
Figure 28:
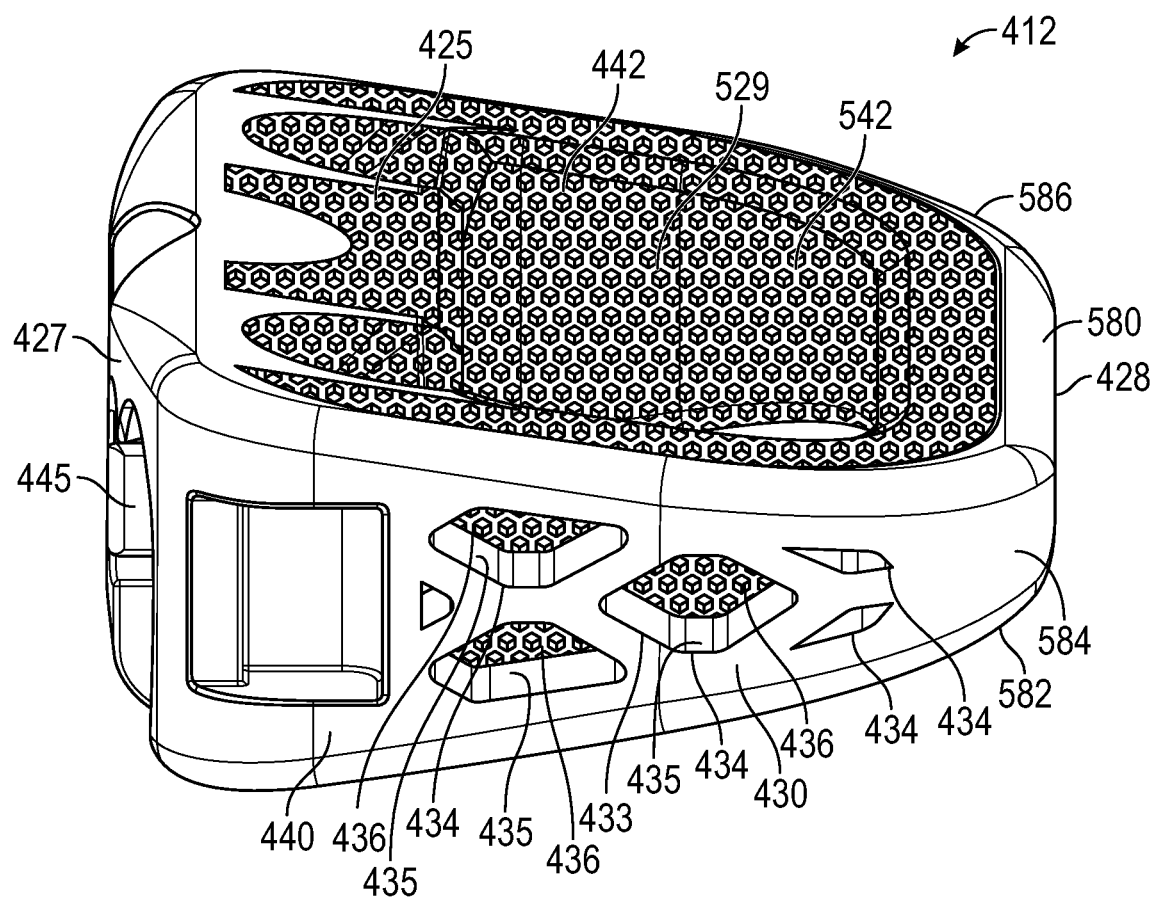
FIG. 28 is another perspective view of the interbody device of FIG. 27 according to an example embodiment.
Figure 34:
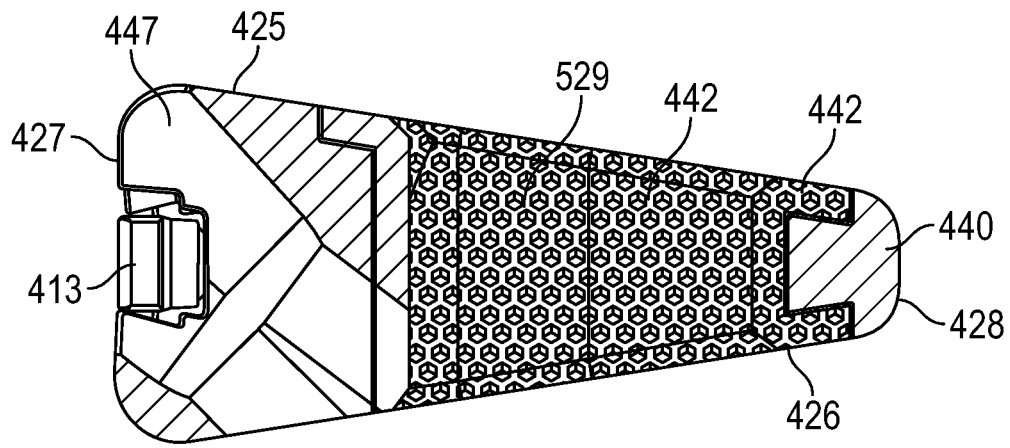
FIG. 34 is a cross sectional view of the interbody device of FIG. 27 taken along line 36 of FIG. 23 according to an example embodiment.
Figure 35:
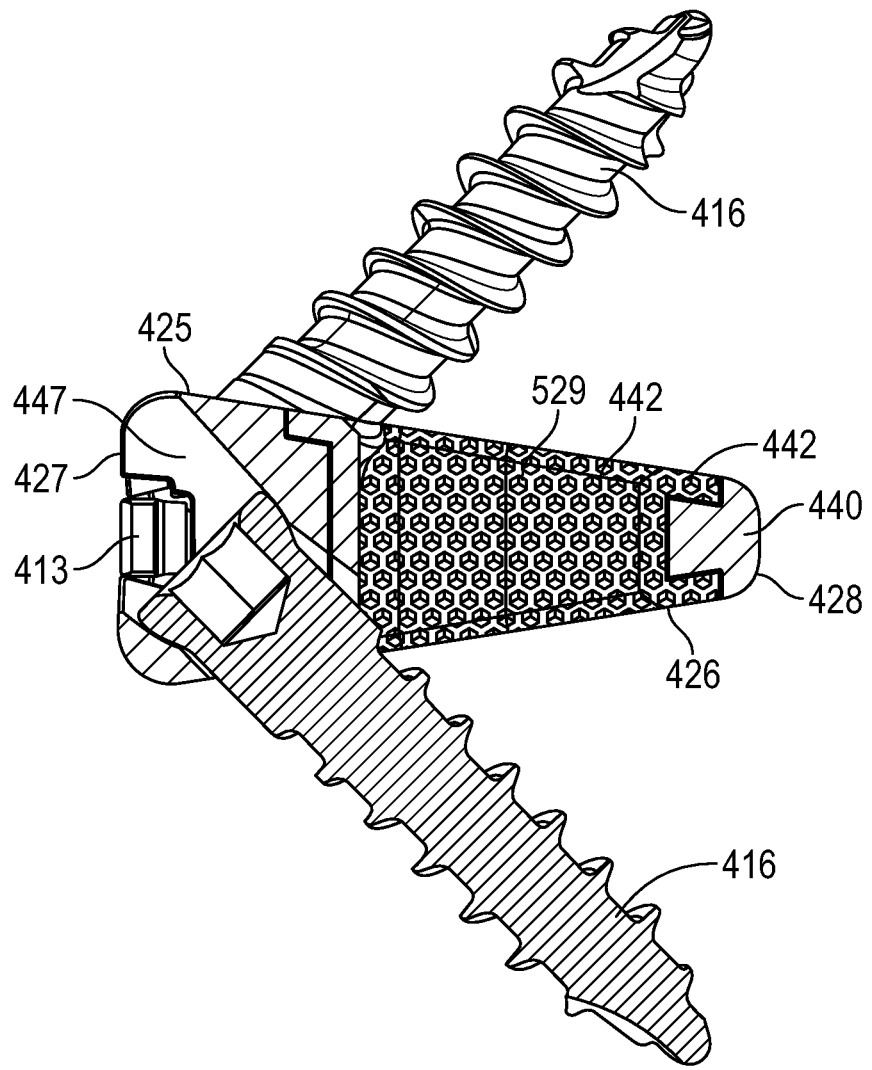
FIG. 35 is a cross sectional view of the implant of FIG. 26 taken along line 36 of FIG. 32 according to an example embodiment.

As seen in FIGS. 27 and 28, the interbody device 412 is generally a rectangular wedge having an upper (superior) surface 425, a lower (inferior) surface 426 (see FIG. 34) opposite to the upper surface 425, a first lateral side 429, a second lateral side 430 that is opposite the first lateral side 429, a first end or front 427, and a second end or rear 428 opposite to the front 427. In some embodiments, the first lateral side 429 and the second lateral side 430 are identical (e.g., mirror images of each other). The nomenclature "first," "second," "third," and "rear" are arbitrary, and not meant to imply any particular orientation of the device. The interbody device 412 also has a cavity 431 that extends from the upper surface 425 to the lower surface 426. The cavity 431 is configured to receive bone graft/bone graft material.

The first lateral side 429 has an inner surface 529 proximate the cavity 431 and an outer surface 629 opposite the inner surface 529. Similarly, the second lateral side 430 has an inner surface 530 proximate the cavity 431 and an outer surface 630 opposite the inner surface 530. The first lateral side 429 and the second lateral side 430 are discussed in greater detail below.

The rear 428 of the interbody device 412 defines a nose or arch having a downwardly angled or sloped upper (superior) surface 580, an upwardly angled or sloped lower (inferior) surface 582 opposite to the downwardly angled upper surface 580, a first rounded side 584, and a second rounded side 586 opposite to the first rounded side 584, the nomenclature "first" and "second" being arbitrary. The front 427 of the interbody device 412 has a slight curvature with two threaded bores 444 (see FIG. 29) that extend therein a distance or to the cavity 431. The threaded bores 444 are configured to receive the cam screws 413.

In certain embodiments, the interbody device 412 may also include a first tool interface 702 and a second tool interface 704. In certain embodiments, the first tool interface 702 and second tool interface 704 may be configured to individually receive a first arm 714 and a second arm 715, respectively, of an installation tool 700. In these example embodiments, the first arm 714 and the second arm 715 may be used to secure the interbody device 412 to the installation tool 700, as will be described further herein.

In some embodiments, the interbody device 412 is manufactured as one piece, although the material need not be homogenous throughout, as will be explained in further detail. For example, in one embodiment, the interbody device 412 will have a solid portion 440 made of a solid biocompatible material and a porous portion 442 made of a porous biocompatible material, such that the porous portion 442 includes a plurality of pores 542. Therefore, solid portion 440 will have a higher density than the porous portion 442.

The solid portion 440 of the interbody device 412 is shown as solid in the figures, while the porous portion 442 is shown with cubic pores 542 in the figures. It should be noted that the cubic pores 542 are not necessarily shown to scale or shape, but instead are simply used to indicate the porous portion 442 of the interbody device 412. Further, while the pores 542 shown in the images are cubic pores 542, it should be appreciated that the pores 542 can be a variety of different shapes, including circular, triangular, square, pentagonal, heptagonal, octagonal, decagonal, etc., or any combination thereof, including irregular shapes and/or patterns.

In certain example embodiments, the pores 542 utilized in the porous portion 442 may be hexagonal in shape due to the relatively high specific strength (i.e. force per unit area at failure divided by its density) of the pores 542. While the interbody device 412 includes a solid portion 440 and a porous portion 442, in one embodiment, the entire interbody device 412 may be manufactured as one piece and/or of a single type material (e.g., titanium). In some embodiments, the interbody device 412 may be manufactured using a 3-D printer that is capable of printing biocompatible material.

In an example embodiment, the porous portion 442 may provide certain benefits relative to other implants. First, the porous portion 442, which substantially surrounds the cavity 431, creates a surface roughness that enhances immediate implant stability and facilitates surface adhesion. For this reason, the inner surfaces 529, 530 are generally porous. Second, the porous portion 442 mimics the structure and porosity of cancellous bone and has a stiffness similar to bone, thereby giving the implant 400 a more comfortable and natural feel for the patient. Third, the porous portion 442 reduces the density of the implant 400 while also enhancing the intraoperative and postoperative imaging, which is discussed further below.

As shown in FIGS. 26-33, the solid portion 440 generally surrounds the porous portion 442 on the first end 427, the second end 428, the first lateral side 429, and the second lateral side 430, such that the material furthest from the cavity 431 on the first end 427, the second end 428, the first lateral side 429, and the second lateral side 430 is generally solid material. However, in the example embodiment shown, the outer surface 629 of first lateral side 429 and the outer surface 630 of the second lateral side 430 include a window lattice 433 (e.g., one or more recesses, windows, etc.). The window lattice 433 is made up of a plurality of lateral windows 434. Each lateral window 434 has a lateral window floor 436 and lateral window walls 435, such that the depth of the lateral window 434 (herein "lateral window depth") (i.e. the distance between the outer surface 629 of the first lateral side 429 and the lateral window floor 436) is substantially equal to the length of the lateral window wall 435 (e.g., measured in a direction perpendicular to the lateral window floor 436). In this embodiment, the solid portion 440 has a thickness equal to the height of the window walls 435 at the edge of each lateral window 434. It should be noted that, for purposes of this application, the window floors 436 are not considered part of the outer surfaces 629, 630. Therefore, the outer surfaces 629, 630 of the first lateral side 429 and the second lateral side 430 are generally solid material.

After the implant 400 has been installed into a patient, the window lattice 433 allows for visualization of the graft area within the cavity 431 and the porous portion 442 using a medical imaging device, such as an X-ray machine or a Fluoroscopy machine. By aiming the medical imaging device substantially parallel to the window walls 435, a medical practitioner or other user is able to view the graft area through the window lattice 433. While the porous portion 442 is positioned between the graft area and the medical imaging device, in some embodiments the porous structure of the porous portion 442 does not substantially prevent X-rays from passing through the porous portion. Therefore, the medical practitioner can use a medical imaging device to view the graft area through the window lattice 433 using the medical imaging device.

The window lattice 433 reduces the overall weight of the interbody device 412 while still providing sufficient structural strength. Since the solid material may be significantly stronger than the porous material, it may provide additional structural strength. Further, by utilizing a window lattice 433 made from solid material, the implant 400 will have increased structural strength while enjoying the several benefits of using a porous material.

Figure 29:
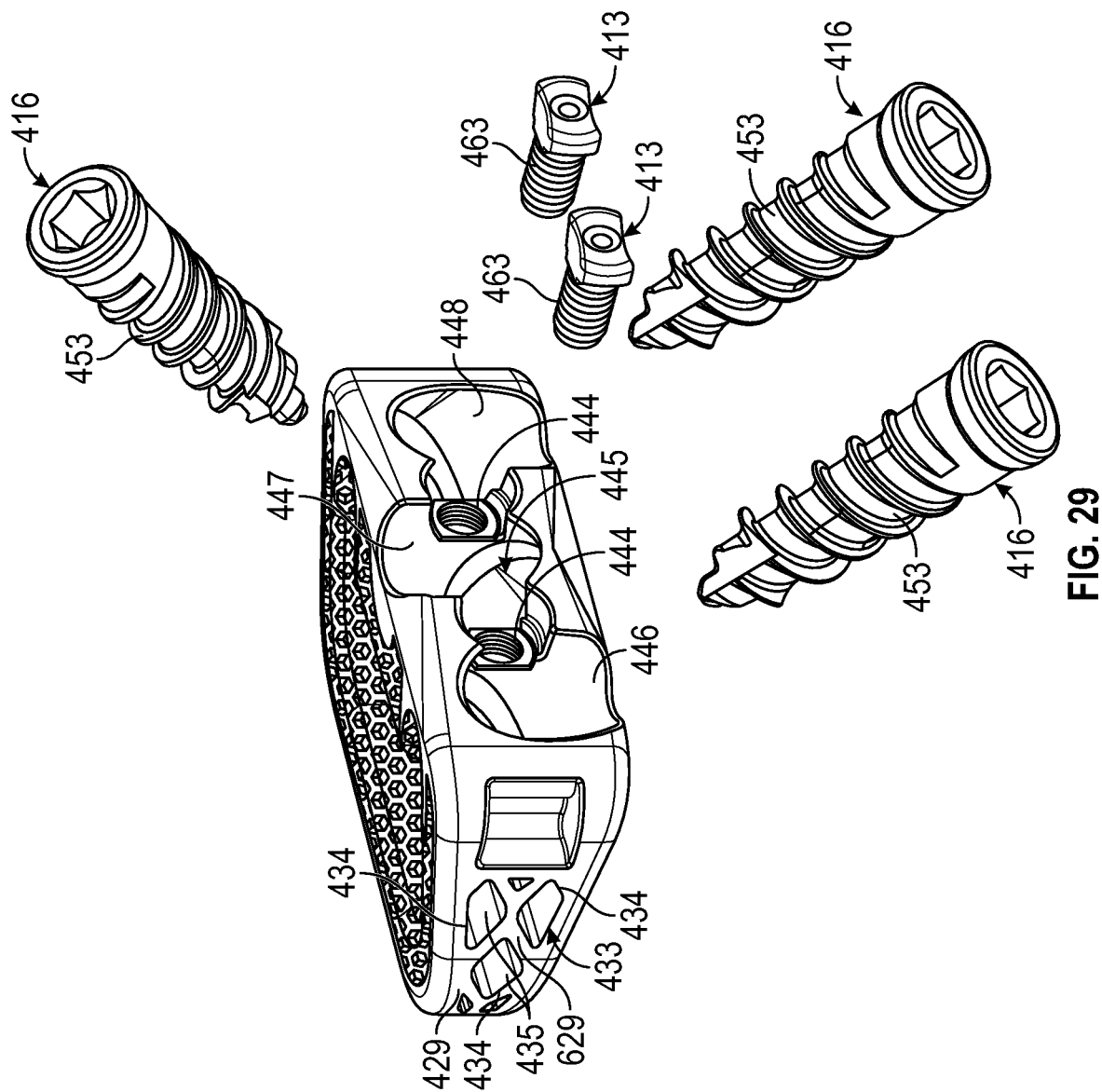
FIG. 29 is an exploded view of the implant of FIG. 26 according to an example embodiment.
Figure 30:
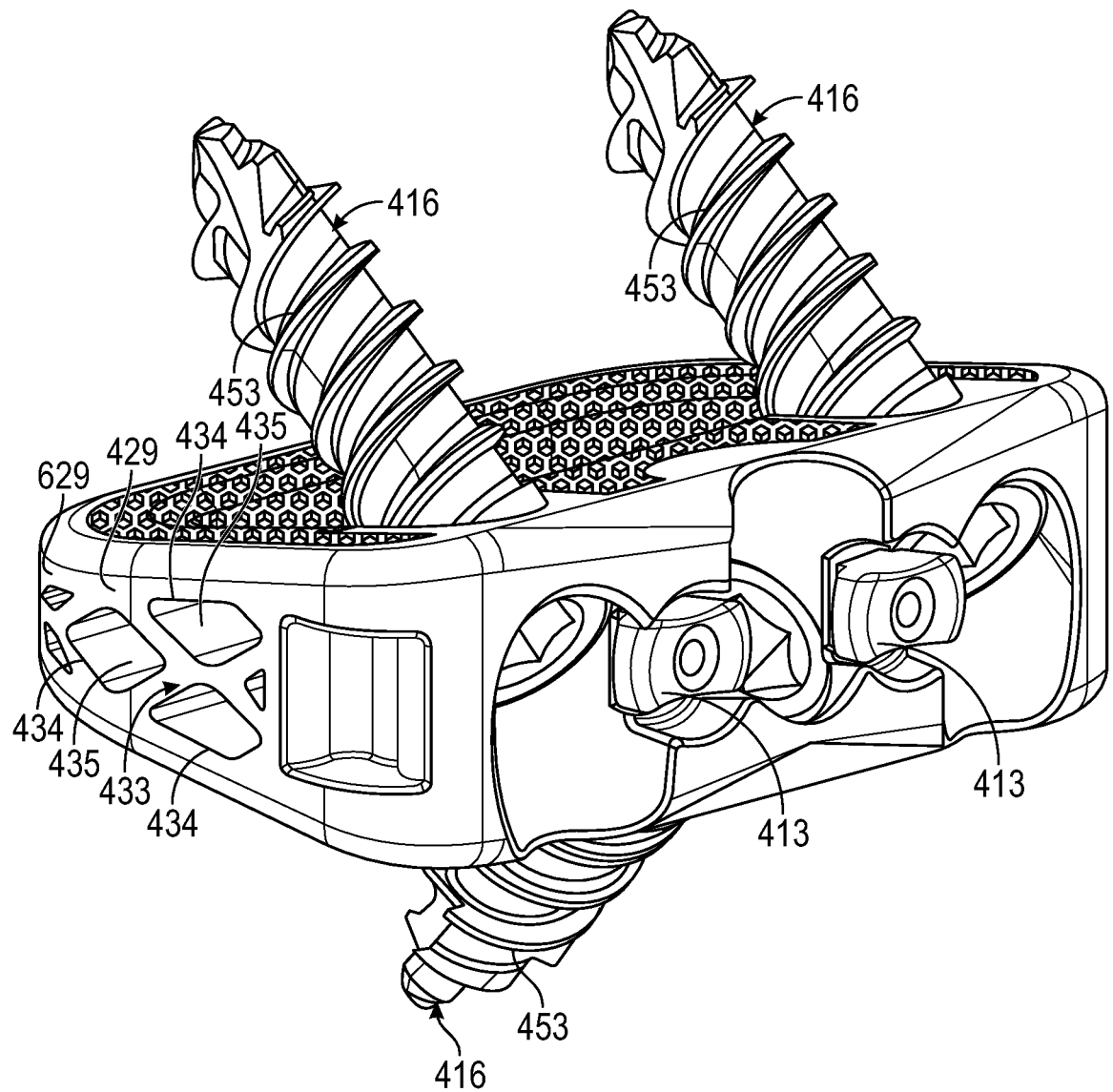
FIG. 30 is another perspective view of the implant of FIG. 26 according to an example embodiment.

Referring now to FIG. 29, an exploded view of the implant 400 is shown. In this example embodiment, the anchoring members 414 are bone screws 416. FIG. 29 shows an exploded view of the implant 400 including an interbody device 412, two cam screws 413, and three bone screws 416.

Figure 36:
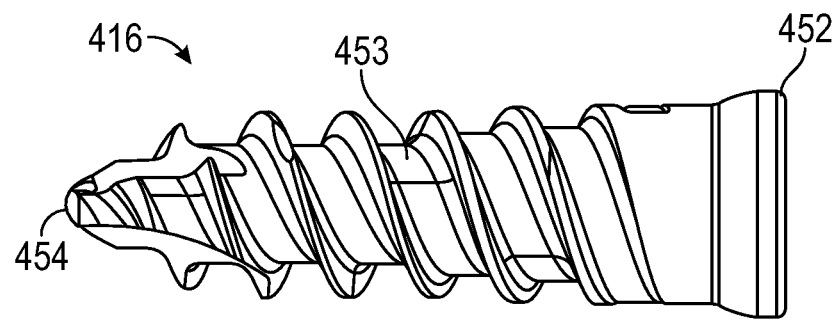
FIG. 36 is a side view of a bone screw according to an example embodiment.
Figure 37:
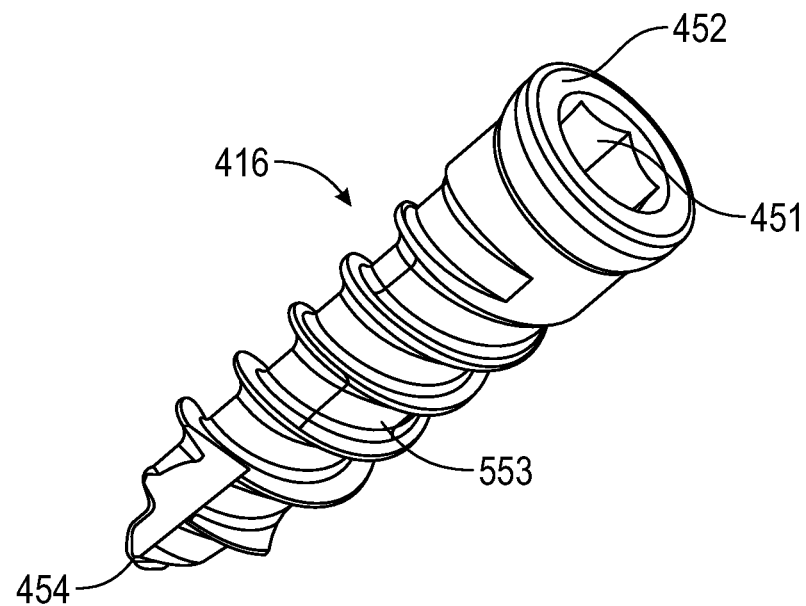
FIG. 37 is a perspective view of the bone screw of FIG. 36 according to an example embodiment.
Figure 38:
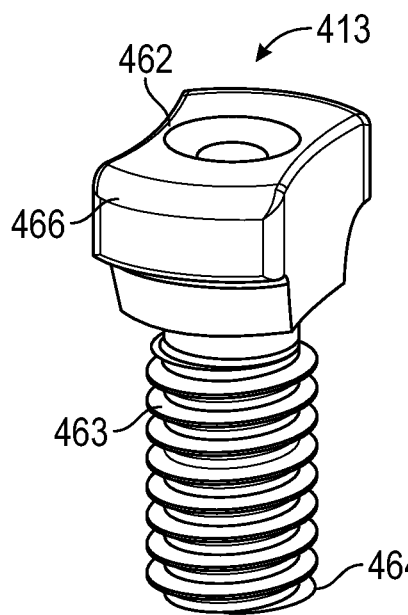
FIG. 38 is a perspective view of a cam screw according to an example embodiment.
Figure 39:
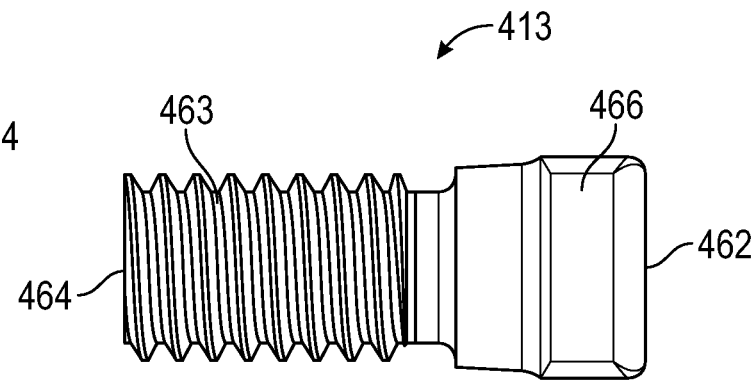
FIG. 39 is a side view of the cam screw of FIG. 38 according to an example embodiment.
Figure 40:
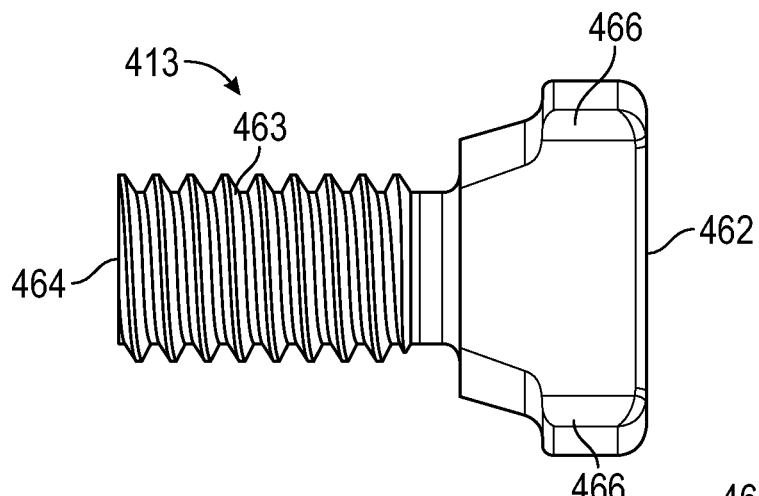
FIG. 40 is another side view of the cam screw of FIG. 38 according to an example embodiment.
Figure 41:
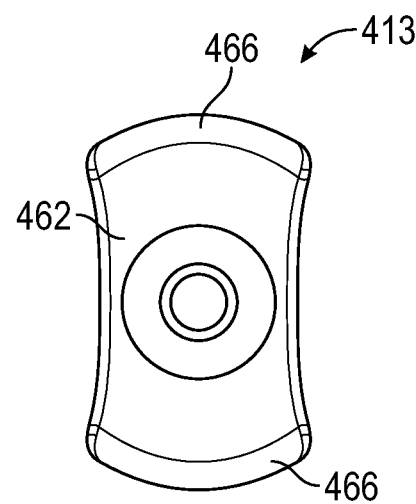
FIG. 41 is a top view of the cam screw of FIG. 38 according to an example embodiment.

As shown in FIGS. 36 and 37, the bone screw 416 includes a linear, externally threaded shaft 453. The bone screw 416 has a head 452 at a first end, and a tip 454 at a second end, the nomenclature first and second being arbitrary. In some embodiments, the tip 454 is pointed. In some embodiments, the diameter of the bone screw 416 gradually decreases from the head 452 to the tip 454. The head 452 further includes a socket 451 configured to receive an installation tool. While this example embodiment shows the socket 451 as being a hex head socket, it should be appreciated that the socket 451 can be designed to receive several different types of hand tools, including a slotted screw driver, a Phillips-head screwdrivers, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

As shown in FIGS. 38-41, the cam screw 413 includes a linear, externally threaded shaft 463. The cam screw 413 has a head 462 at a first end, and a tip 464 at a second end, the nomenclature first and second being arbitrary. In this example embodiment, the tip 464 is flat. In this example embodiment, the diameter of the shaft 463 remains constant throughout. The head 462 also includes two shoulders 466 positioned at opposite sides of the head 462. The shoulders 466 extend radially from the center of the head 462, such that the distance from the center of the head 462 to the edge of the shoulder 466 is greater than the radius of the threaded shaft 463.

As shown in FIG. 29, the first end 427 of the interbody device 412 includes a channel 445 that extends generally from adjacent the first lateral side 429 to adjacent the second lateral side 430. The channel 445 includes a first angled screw bore 446 in the first end 427 of the interbody device 412 proximate the first lateral side 429. The first angled screw bore 446 extends from the first end 427 to the cavity 431. The first angled screw bore 446 is sized to allow the threaded shaft 453 of the bone screw 416 to extend therethrough and into the cavity 431. The front of the first angled screw bore 446 defines a pocket sized countersink to capture the bone screw head 452. The first angled screw bore 446 is angled upwardly such that the threaded shaft 453 and thus the tip 454 of the bone screw 416 extends upwardly out of the cavity 431.

The channel 445 further includes a second angled screw bore 447 in the first end 427 of the interbody device 412 proximate a middle of the first end 427. The second angled screw bore 447 extends from the first end 427 to the cavity 431. The second angled screw bore 447 is sized to allow the threaded shaft 453 of the bone screw 416 to extend therethrough and into the cavity 431. The front of the second angled screw bore 447 defines a pocket sized countersink to capture the bone screw head 452. The second angled screw bore 447 is angled downwardly such that the threaded shaft 453 and thus the tip 454 of the bone screw 416 extends downwardly out of the cavity 431.

The channel 445 further includes a third angled screw bore 448 in the first end 427 of the interbody device 412 proximate the second lateral side 430. The third angled screw bore 448 extends from the first end 427 to the cavity 431. The third angled screw bore 448 is sized to allow the threaded shaft 453 of the bone screw 416 to extend therethrough and into the cavity 431. The front of the third angled screw bore 448 defines a pocket sized countersink to capture the bone screw head 452. The third angled screw bore 448 is angled upwardly such that the threaded shaft 453 and thus the tip 454 of the bone screw 416 extends upwardly out of the cavity 431.

It should be appreciated that the angle of the bores may be changed as desired. In addition, in this example embodiment, the angled screw bores allow for variable trajectory of the bone screws 416. For example, in this embodiment, the first angled screw bore 446 and the third angled screw bore 448 allow a variable upwards trajectory of the bone screw 416 of up to forty-five degrees from the horizontal mid-plane of the interbody device 412. Further, in this example embodiment, the second angled screw bore 447 allows a variable downward trajectory of the bone screw 416 of up to 45 degrees from the horizontal mid-plane of the interbody device 412. In other embodiments, other trajectories may be used (e.g., 30 degrees, etc.), the trajectories relative to the horizontal mid-plane may be constant or vary between the different screw bores.

The first end 427 of the interbody device 412 also includes two threaded bores 444 in the channel 445. The threaded bores 444 are configured to receive a cam screw 413. In this example embodiment, the threaded bores 444 extend from the first end 427 into the solid portion 440 of the interbody device 412. In this example embodiment, the threaded bores 444 do not extend into the porous portion 442 or into the cavity 431. However, in other example embodiments, the threaded bores 444 may extend into the porous portion 440 and/or into the cavity 431. Further, in this embodiment, the threaded bores 444 are substantially parallel to the horizontal mid plane of the interbody device 412. In other embodiments, the threaded bores 444 may be angled up or down relative to the horizontal mid plane of the interbody device 412.

Figure 31:
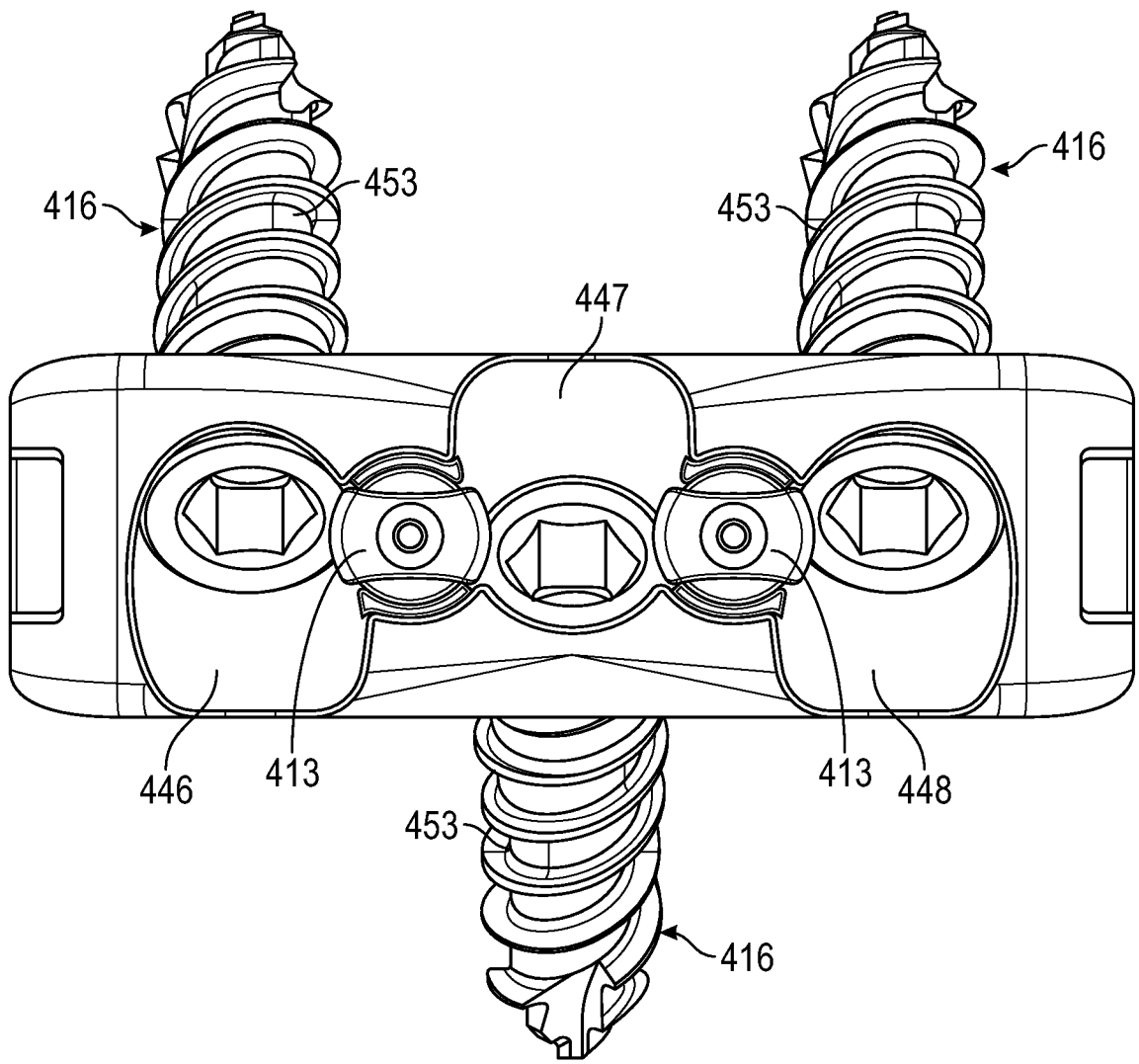
FIG. 31 is a front view of the implant of FIG. 26 according to an example embodiment.
Figure 32:
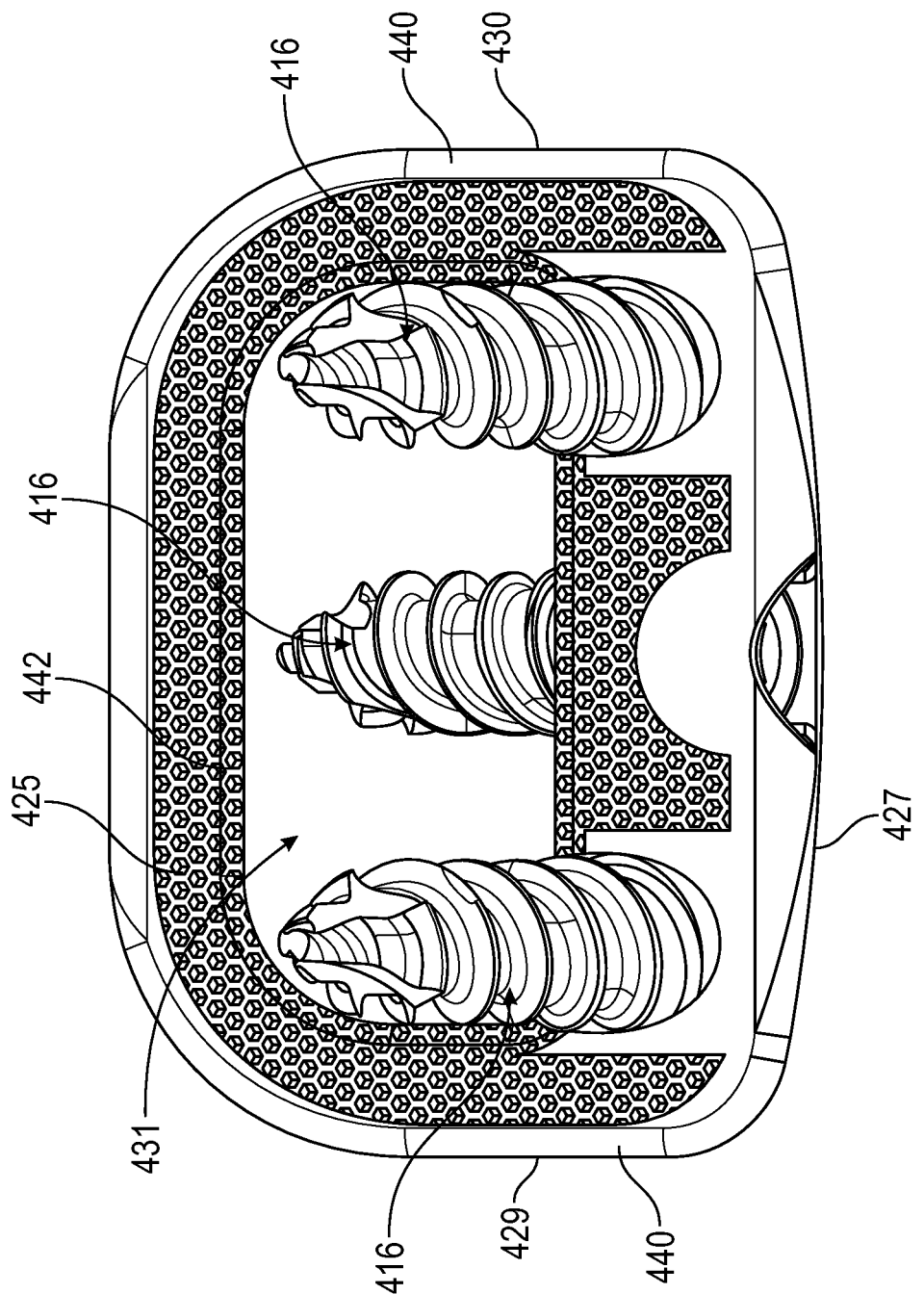
FIG. 32 is a top view of the implant of FIG. 26 according to an example embodiment.
Figure 33:
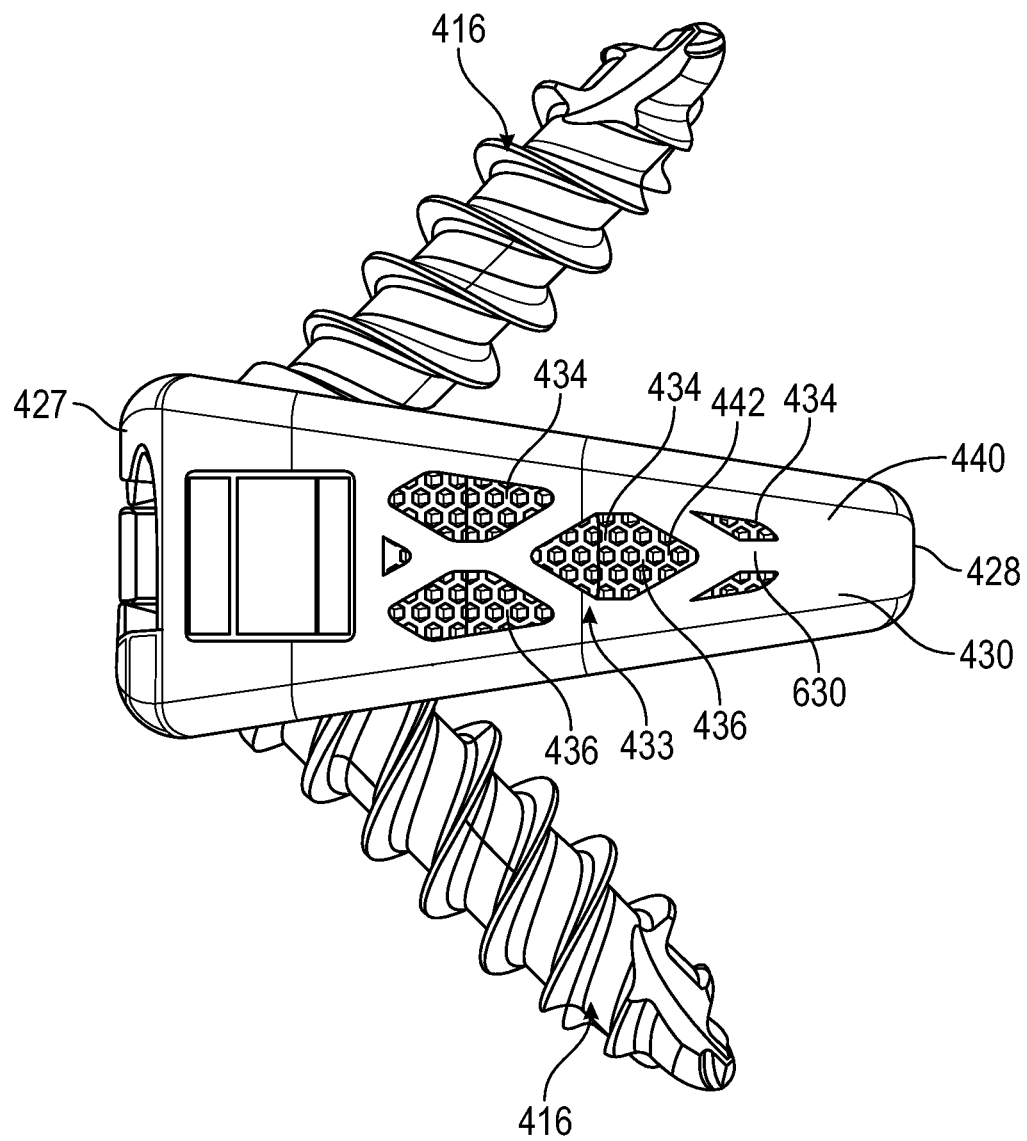
FIG. 33 is a side view of the implant of FIG. 26 according to an example embodiment.

Prior to surgery, the cam screws 413 can be pre-threaded into the threaded bores 444 of the interbody device 412 as shown in FIG. 27. When screwed into a first position, the shoulders 466 of the cam screws 413 do not reduce the clearance area of the first angled screw bore 446, the second angled screw bore 447, or the third angled screw bore 448, thereby allowing a surgeon or other user to drive anchoring members 414 into the vertebral bodies above and below the interbody device 412 while the cam screws 413 are pre-threaded into the interbody device 412. Once the anchoring members 414 are anchored into the vertebral bodies above and below the interbody device 412, a surgeon may then adjust or rotate the cam screws 413 approximately a quarter of a turn, into a second position, as shown in FIG. 31. In one embodiment, once the cam screws 413 are tightened approximately a quarter of a turn, the shoulders 466 will bottom out against the head 452 of the anchoring members 414. In doing so, the shoulder 466 of the cam screw 413 will prevent back-out of the anchoring member 414.

Figure 42:
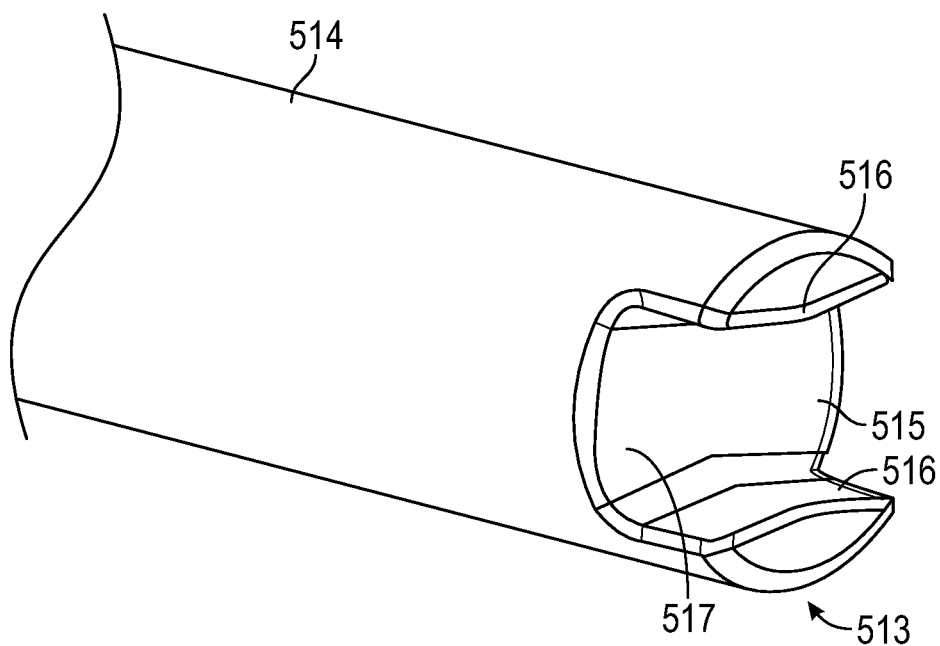
FIG. 42 is a perspective view of a portion of a cam tool according to an example embodiment.
Figure 43:
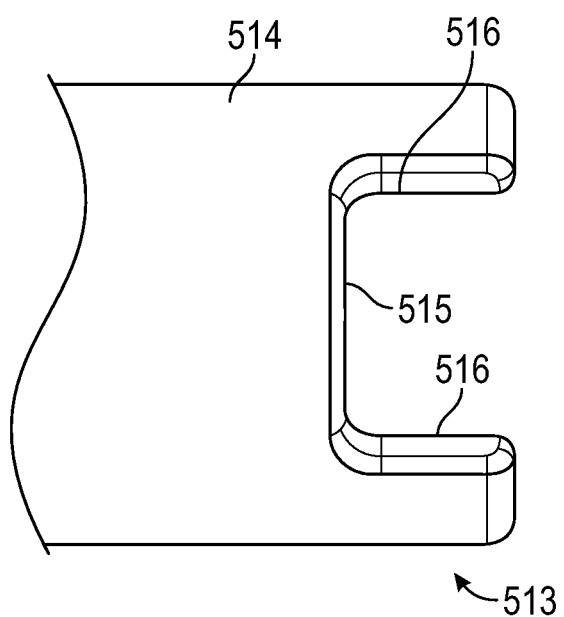
FIG. 43 is a side view of a portion of the cam tool of FIG. 42 according to an example embodiment.
Figure 44:
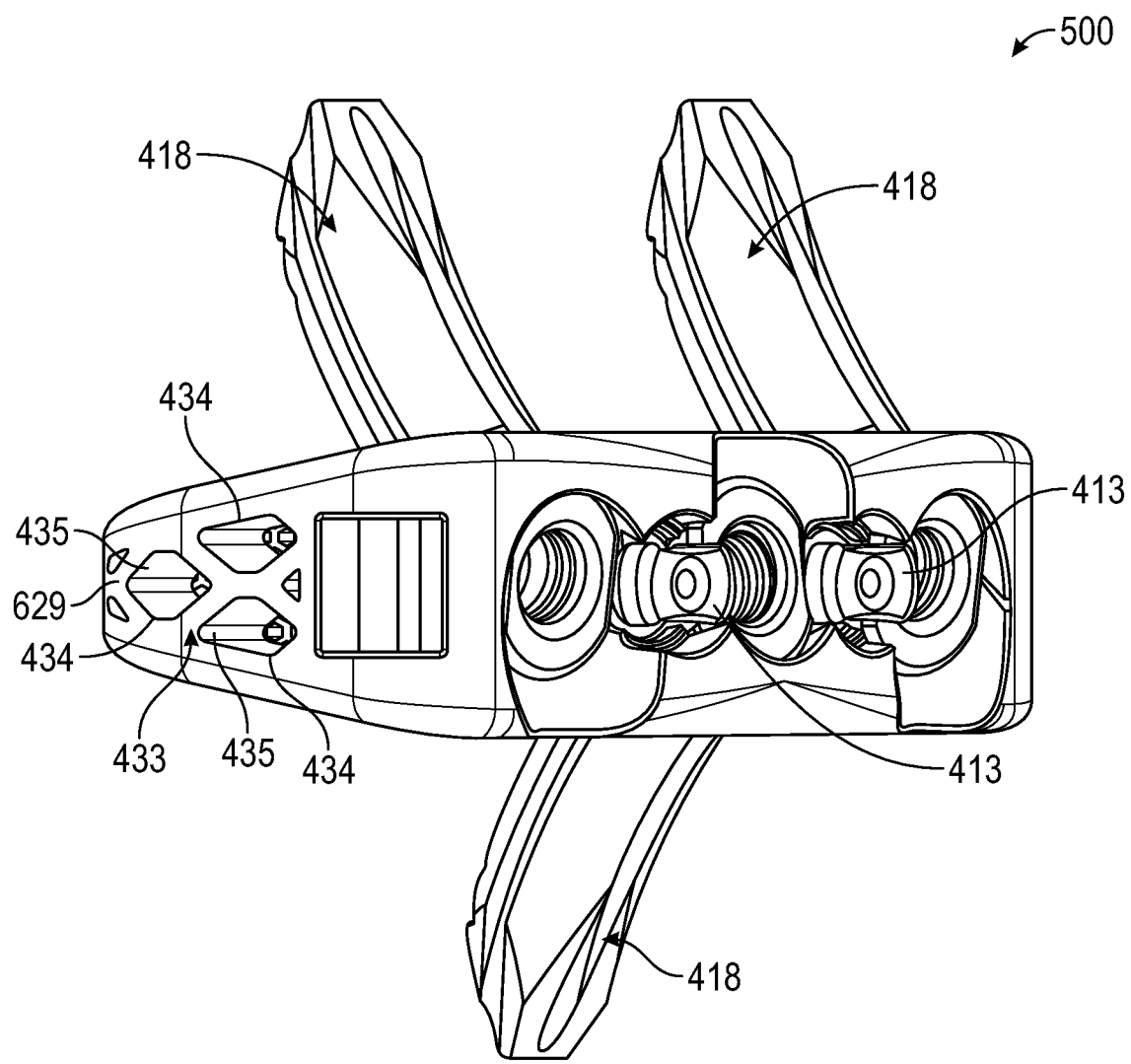
FIG. 44 is a perspective view of an implant according to another example embodiment.

In one embodiment, the cam screw 413 may be tightened using a cam tool 513 shown in FIGS. 42-43. In one embodiment, the cam tool 513 includes a shaft 514 and a cam screw interface 515 at one end of the shaft 514. The cam screw interface 515 includes a first shoulder 516a and a second shoulder 516b. In this example embodiment, the first shoulder 516a and the second shoulder 516b are identical (e.g., mirror images). The cam screw interface 515 also includes a cam screw seat 517. The cam screw seat 517 is configured to receive the head 462 of the cam screw 413, such that the shoulders 516 of the cam tool 513 engage with the shoulders 466 of the cam screw 413 when a torque is applied to the cam tool 513. In doing so, the cam tool 513 can be used to turn the cam screw 413 while the cam screw 413 is threaded into the interbody device 412.

In other embodiments, the cam screw 413 may be turned using other types of tools. For example, the cam screw 413 can be designed to receive several different types of drivers, including a slotted screw driver, a Phillips-head screwdrivers, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Using cam screws 413 to prevent back-out of anchoring members 414 as described herein may provide certain benefits relative to other implants. First, due to the unique shape of the head 462, the cam screws 413 can be partially screwed into the interbody device 412 prior to surgery without reducing the clearance of the first angled screw bore 446, the second angled screw bore 447, or the third angled screw bore 448. Since the surgeon does not need to turn the cam screw 413 several full turns, surgery time is reduced. Additionally, since the cam screw 413 only needs to be turned approximately a quarter of a turn to prevent back-out of the anchoring members 414, it will be easier for the surgeon to know when the cam screw 413 is fully screwed into place. Further, due to the unique shape of the head 462, it will be obvious to the surgeon when the shoulder 466 is correctly positioned to prevent back-out of the anchoring member 414.

Referring now to FIGS. 44-47, an implant 500 (e.g., an anterior lumbar interbody fusion (ALIF) implant (ALIF spine implant or ALIF implant)) is shown according to one embodiment. Implant 500 is made from a biocompatible material such as, but not limited to, PEEK, PETE, other plastic or polymer, titanium, stainless steel, an alloy of titanium or stainless steel, or otherwise, or any combinations thereof. In some embodiments, the implant 500 is 3-D printed. In other example embodiments, the implant 500 may be machined, cast, or manufactured using any combination of 3-D printing, machining, casting, etc. The implant 500 may use many of the same of similar components as the implant 400. For example, the implants may use the same interbody device and cam screws, and differ in the type of anchoring elements used. In an example embodiment, the implant 500 includes an interbody device 412 and two or more bone barbs 418. In certain embodiments, the implant 500 also includes at least one cam screw 413.

As shown in FIGS. 45-47, the bone barb 418 is characterized by a curved shaft 473 having a constant diameter, but other configurations may be used. The bone barb 418 has a head 472 at a first end, and a tip 474 at a second end, the nomenclature first and second being arbitrary. In this example embodiment, the tip 474 is beveled, but other configurations may be used. The head 472 includes a threaded socket 475 in its upper surface that is configured to receive an installation tool. The underside of the head 472 further includes a rounded shoulder 476 that bottoms out against the interbody device 412 when the bone barb 418 is fully inserted into the first angled screw bore 446, the second angled screw bore 447, or the third angled screw bore 448. The head 472 also has a flat 477 on one side and another flat on the other side. A plurality of grooves (or similar feature) 480, 481, 482, 483 are provided on the outside surface of the bone barb 418. In one embodiment, four grooves are provided, while in other embodiments fewer or more grooves may be provided (e.g., 3, 5, etc.). In this example embodiment, the grooves 480, 481, 482, 483 extend from the tip 474 to the head 472. The grooves reduce the cross-sectional area of the barbs thereby reducing the amount of material (bone) that has to be displaced in order for the barbs to be impacted into the vertebral bone. Further, the bone barb 418 has a plurality of serrations 478 on the surface of the curved shaft 473. These serrations 478 improve the stability of the bone barb 418 when inserted into the vertebral bone and assist in preventing back-out of the bone barb 418.

It should be appreciated that the first angled screw bore 446, the second angled screw bore 447, and the third angled screw bore 448 of the interbody device 412 are configured to receive the bone barbs 418 in a similar manner as the bone screws 416. Therefore, the bone barbs 418 may be used with the interbody device 412 according to the disclosure above.

Referring now to FIGS. 48-56, an installation tool 700 is shown according to an example embodiment. In certain embodiments, the installation tool 700 may be used to insert or install an implant 750 and anchoring members into a patient. The implant 750 may be or share similar features with any other implants described herein. For example, in one embodiment, the installation tool 700 is used with implant 400. In certain embodiments, the implant 750 is substantially similar to the implant shown in FIG. 44, except as described herein. In other embodiments, the implant 750 may be comprised entirely of solid material or may be comprised entirely of porous material. In certain embodiments, the implant 750 may be any implant configured to be installed using the installation tool 700, as will be described herein.

Figure 48:
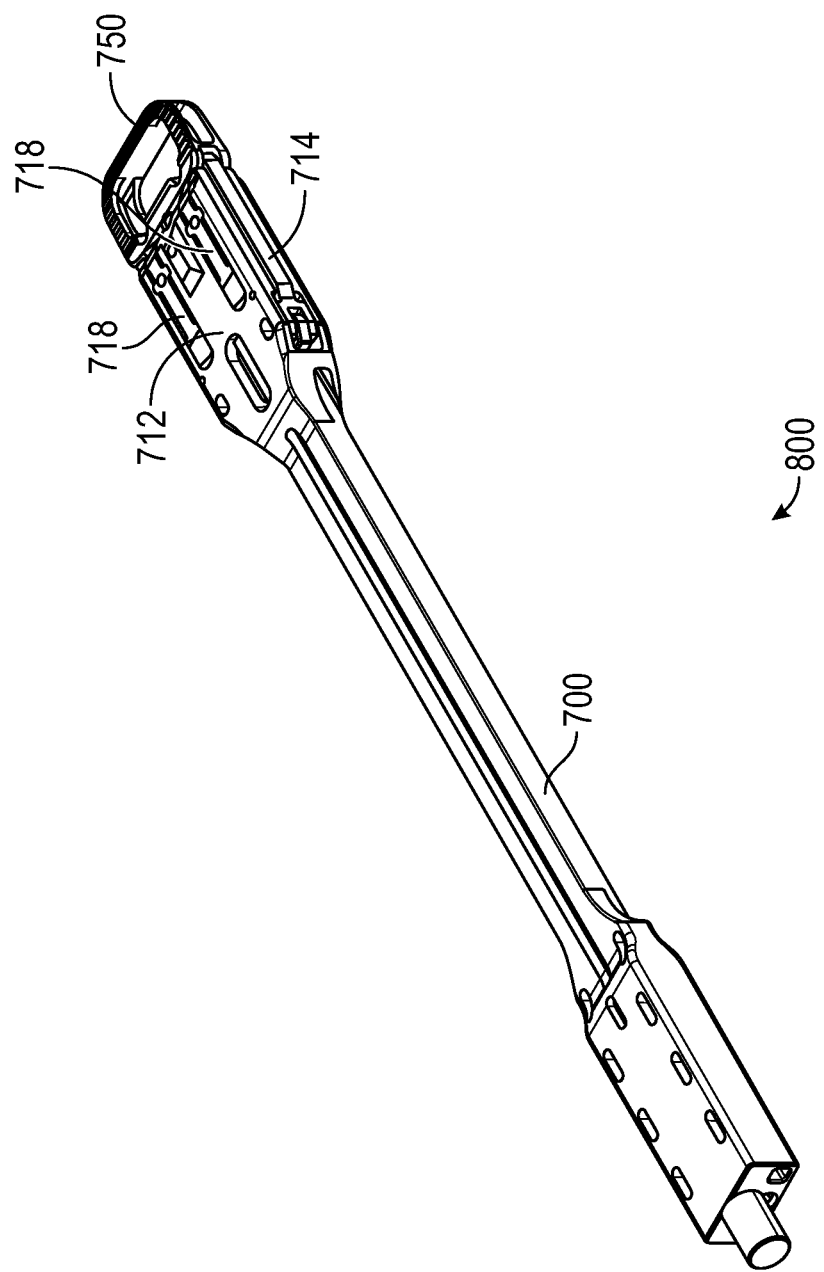
FIG. 48 is a perspective view of an installation assembly according to an example embodiment.
Figure 49:
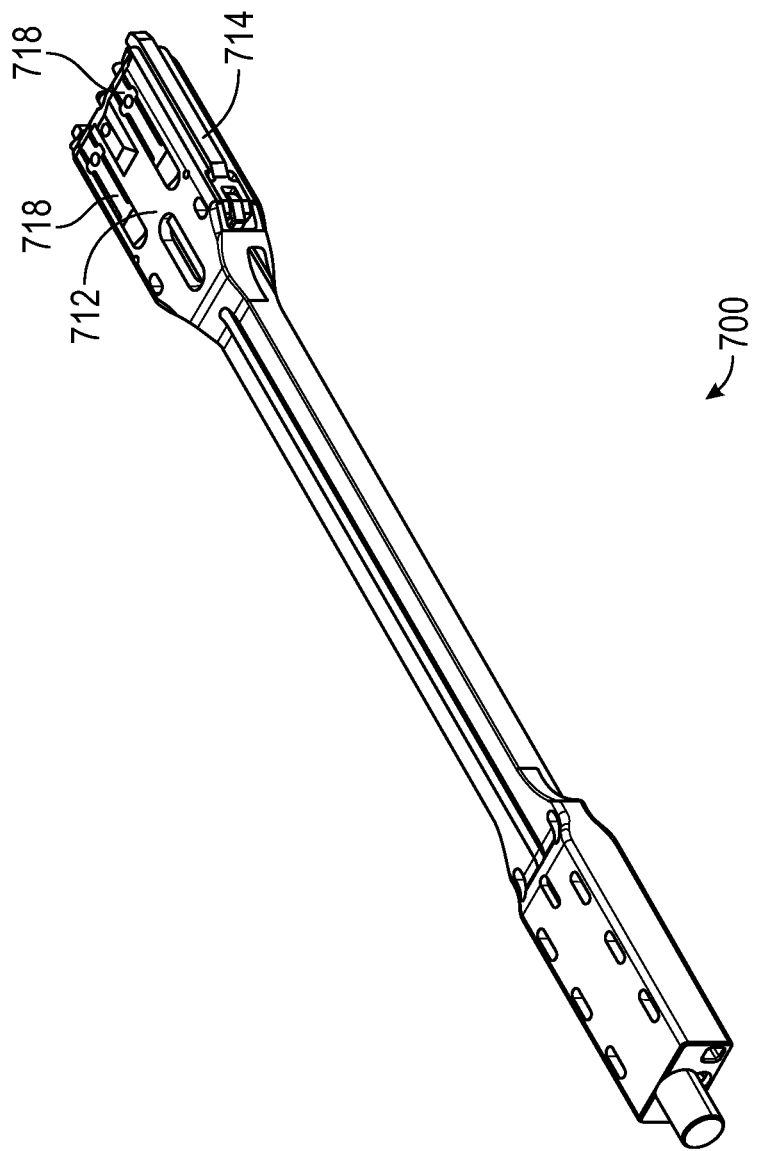
FIG. 49 is a perspective view of an installation tool according to an example embodiment.
Figure 51:
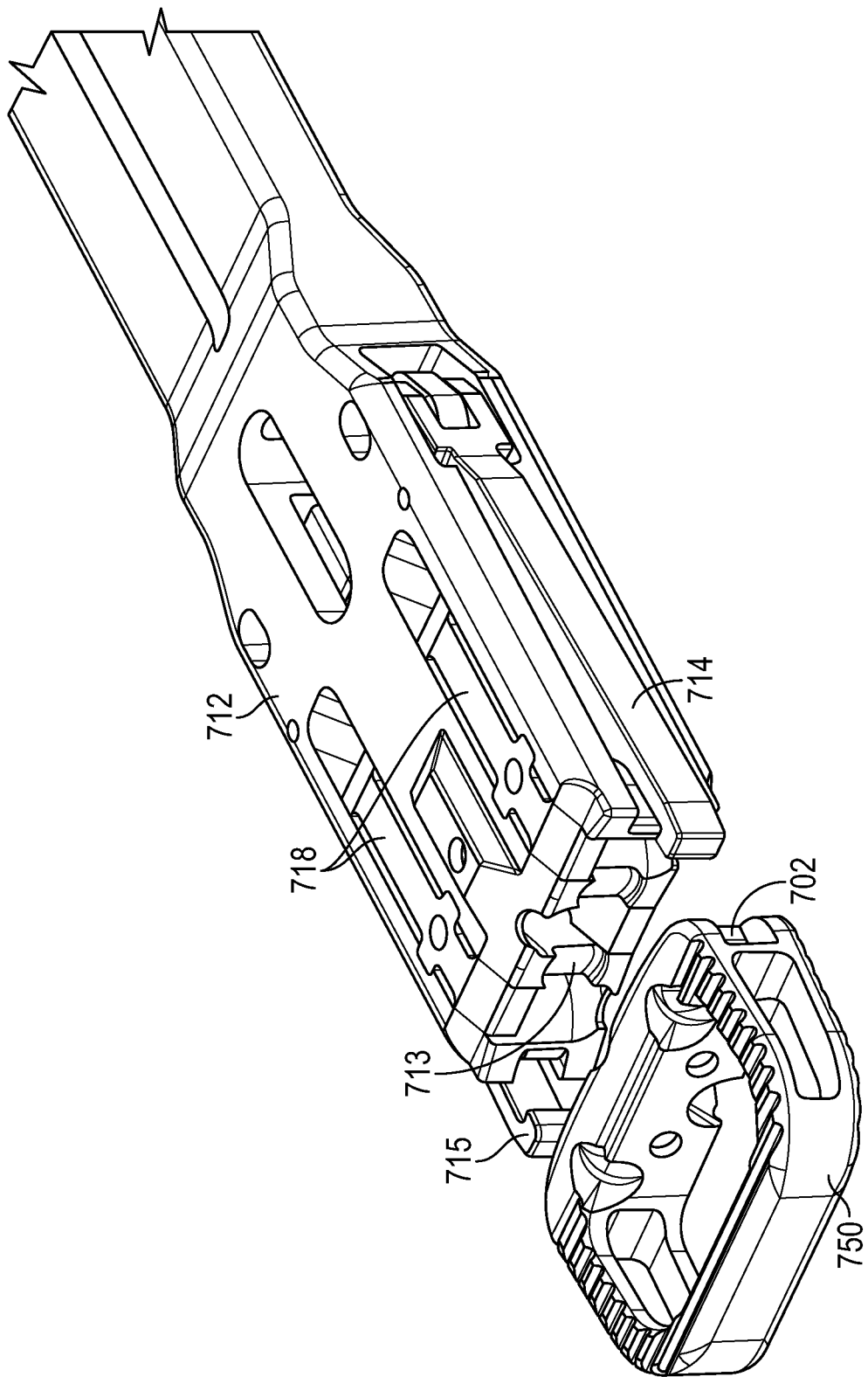
FIG. 51 is a partial perspective view of an installation assembly according to an example embodiment.

As shown in FIG. 48, the installation tool 700 may be configured to receive an implant 750, the installation tool 700 and implant 750 forming an installation assembly 800 (see FIG. 51). For example, as shown in FIG. 48, the installation tool 700 may controllably receive an implant 750, such that the implant 750 is controllably attached to the installation tool 700. Further, as shown in FIG. 49, the installation tool 700 may include a retention member that may controllably release the implant 750 as will be described further herein. In certain embodiments, the retention member may include the first arm 714 and the second arm 715.

Figure 50:
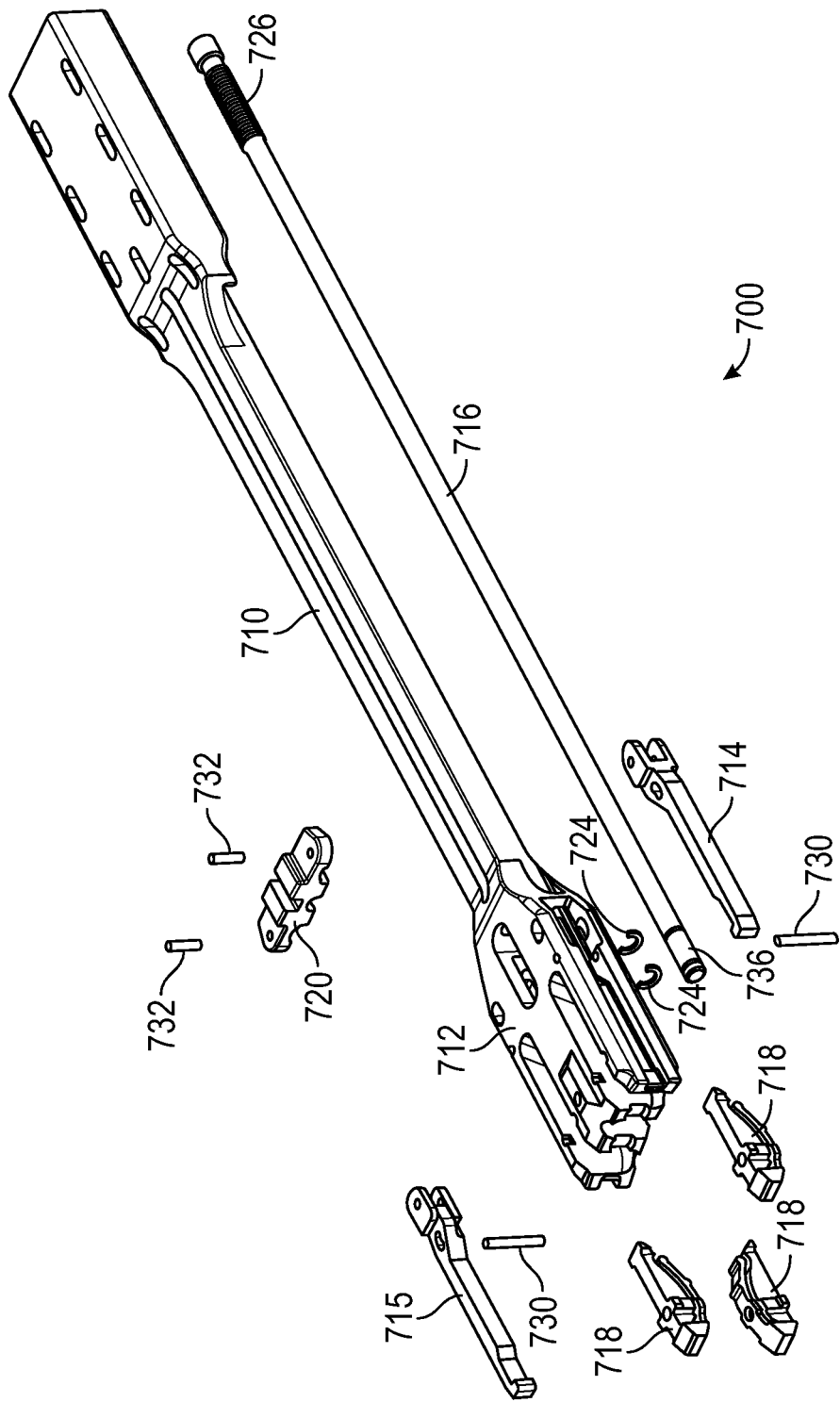
FIG. 50 is an exploded view of the installation tool of FIG. 49 according to an example embodiment.

FIG. 50 shows an exploded view of the installation tool 700 according to an example embodiment. In this example embodiment, the installation tool 700 includes a tool body 710, which further includes an interface body 712. The installation tool 700 further includes a first arm 714 and a second arm 715 positioned opposite the first arm 714 across the interface body 712. In certain embodiments, the first arm 714 and the second arm 715 may be used to secure the implant 750 to the interface body 712 as will be described further herein. In certain embodiments, the first arm 714 is identical to the second arm 715. In other embodiments, the first arm 714 is a mirror image of the second arm 715.

According to certain embodiments, the installation tool 700 further includes a control shaft 716 disposed within the installation tool body 710. The control shaft 716 may include a threaded shaft 726 near a first end, and a plate interface 736 positioned near a second end, opposite the first end. In certain embodiments, the threaded shaft 726 may engage with a threaded bore located inside the installation tool body 710, such that rotating the control shaft 716 will cause the threaded shaft 726 to rotate within the threaded bore inside the installation tool body. Further, rotating the control shaft 716 will also cause the control shaft 716 to translate linearly within the installation tool body 710, as will be described further herein. Further, the plate interface 736 is configured to receive a control plate 720, which is secured to the control shaft 716. In certain embodiments, the control plate is 720 is secured to the plate interface 736 using two retention rings 724. In an example embodiment, the retention rings 724 are horseshoe retention rings, however, the control plate 720 may be secured to the control shaft 716 using any type of retention ring, such as a welding ring, c-clips, or any other type of retaining ring or other structure.

The installation tool 700 may further include a plurality of spring members 718. For example, the spring members 718 may be leaf spring in an example embodiment. The plurality of spring members 718 may be used to retain a plurality of anchoring members within the interface body 712, as will be described further herein. In certain embodiments, the spring members 718 may be welded to the interface body 712. In other embodiments, the spring members 718 may be secured to the interface body 712 using other means, such as an adhesive, or the spring members 718 may be secured to the interface body 712 using a screw or nut and bolt. In this example embodiment, the installation tool 700 may also include a plurality of pins 730, 732. In this embodiment, the pins 730 may be used to secure the first arm 714 and the second arm 715 to the interface body 712. Further, the two pins 732 may be used to secure the control plate 720 within the interface body 712, such that the control plate 720 may translate linearly within the interface body 712 in response to the control shaft 716 being turned, as will be described further herein.

Figure 52:
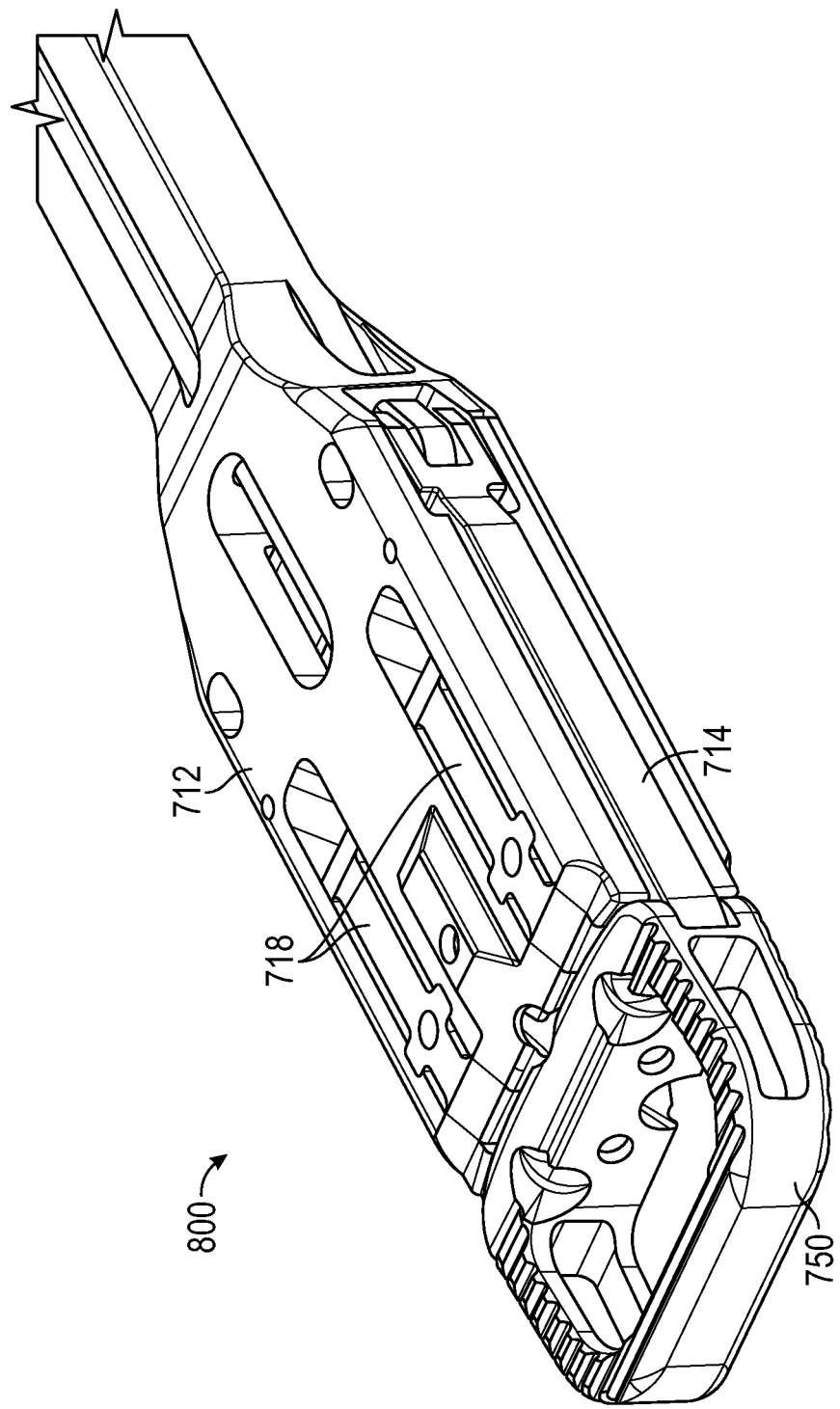
FIG. 52 is a partial perspective view of the installation assembly of FIG. 48 according to an example embodiment.

Referring now to FIGS. 51 and 52, an example embodiment of the installation assembly 800 is depicted. In this example embodiment, the implant 750 is secured to the interface body 712. More specifically, in certain embodiments, the interface body 712 may have an interface face 713 configured to receive the face of the implant 750. For example, the interface face 713 may include cutout slots for the cam screws 413 (see FIG. 31) located on the face of an implant 750. Further, the interface face 713 may include slots configured to let anchoring members pass from the interface body 712, through the implant 750, and into an adjacent bone, as will be described further herein.

Figure 53:
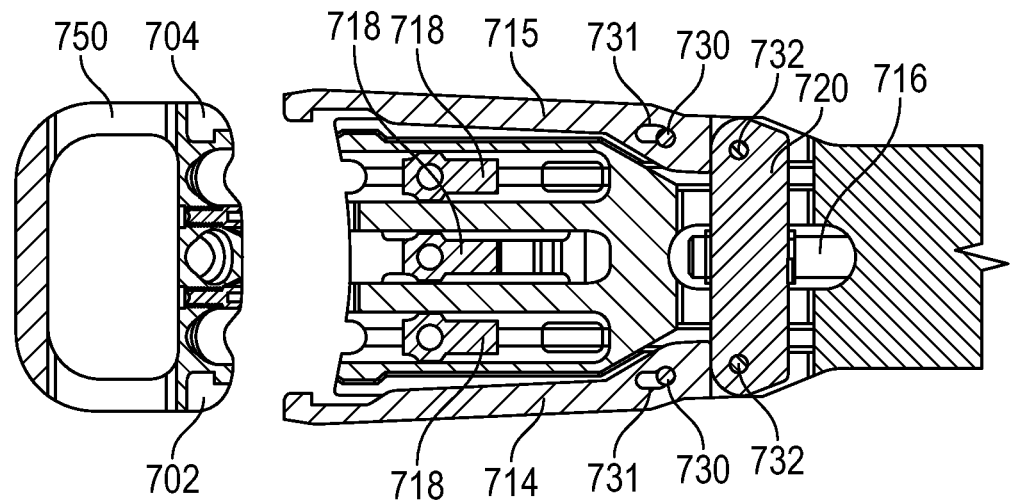
FIG. 53 is a cross-section view of the installation assembly of FIG. 51 according to an example embodiment.
Figure 54:
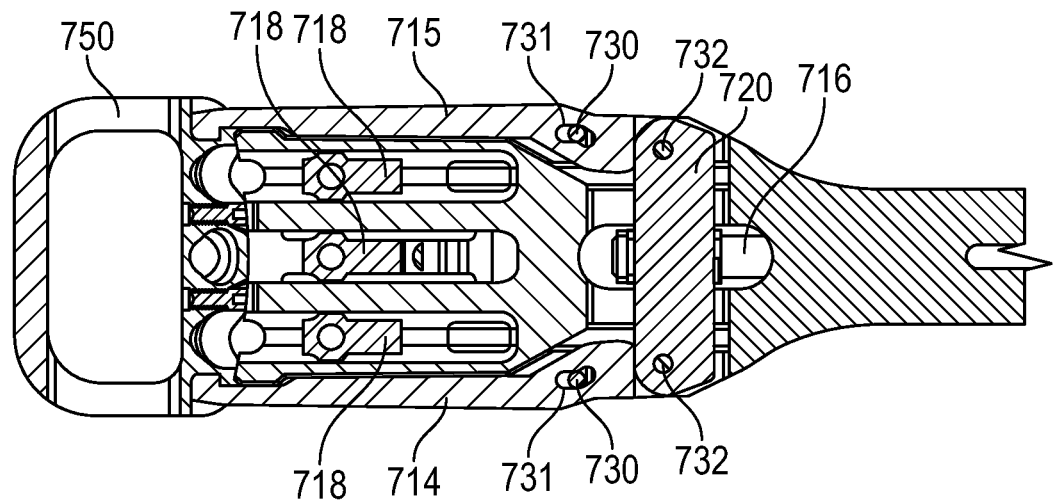
FIG. 54 is a cross-section view of the installation assembly of FIG. 52 according to an example embodiment.

Referring now to FIGS. 53 and 54, cross-section views of the interface body 712 are shown according to an example embodiment. In this example embodiment, the implant 750 has a first tool interface 702 and a second tool interface 704 configured to receive the first arm 714 and the second arm 715, respectively. In this example embodiment, the first arm 714 and the second arm 715 are used to secure the implant 750 to the installation tool 700.

In certain embodiments, the arms 714, 715 are controllably movable from a first, open position, as shown in FIG. 53, to a second, closed position shown in FIG. 54, and every position there in between. In certain example embodiments, the position of the arms 714, 715 is controlled using the control shaft 716. In example embodiments, the control plate 720 is secured to the control shaft 716 using pins 732 and retention rings 724, such that the control plate 720 will move linearly proportionally to the control shaft 716 moving linearly within the tool body 710. In an example embodiment, the control shaft 716 may be turned, such that the threaded shaft 726 rotates within a threaded bore inside the tool body 712, and the plate interface 736 rotates within the control plate 720. As the threaded shaft 726 rotates within the threaded bore, the control shaft 716 and control plate 720 will also translate linearly within the installation tool 700. For example, in certain embodiments, when the control shaft 716 is turned in a clockwise direction, the control plate 720 will move in a direction towards the interface face 713, and when the control shaft 716 is turned in a counter-clockwise direction, the control plate 720 will move in a direction away from the interface face 713.

In certain embodiments, the control plate 720 is also connected to the first arm 714 and the second arm 715 using pins 732. In this example embodiment, the pins are inserted (e.g. using a press fit, friction fit, slip fit, etc.) into bores in the control plate 720 and bores in the arms 714, 715. The arms 714, 715 further include a pin slot 731 configured to receive a pin 730, such that the pin 730 may translate within the pin slot 731. In certain example embodiments, the interface body 712 further includes bores configured to receive the pins 730, such that the pins 730 may be inserted (e.g. using a press fit or friction fit) into the interface body 712 and through the pin slot 731 of the arms 714, 715.

In certain embodiments, when the control shaft 716 is turned in a direction that causes the control plate 720 to translate in a direction towards the interface face 713, the arms 714, 715 will move into an open position, until the pin 730 bottoms out in the pin slot 731, as shown in FIG. 53. In this position, the implant 750 may be received by the installation tool 700 at the interface face 713. Then, in certain embodiments, the control shaft 716 may be rotated such that the control plate 720 will translate in a direction away from the interface face 713. In doing so, the arms 714, 715 will move into a closed position, as shown in FIG. 54, until the arms 714, 715 bottom out within the tool interfaces 702, 704, thereby securing the implant 750 to the installation tool 700.

Figure 55:
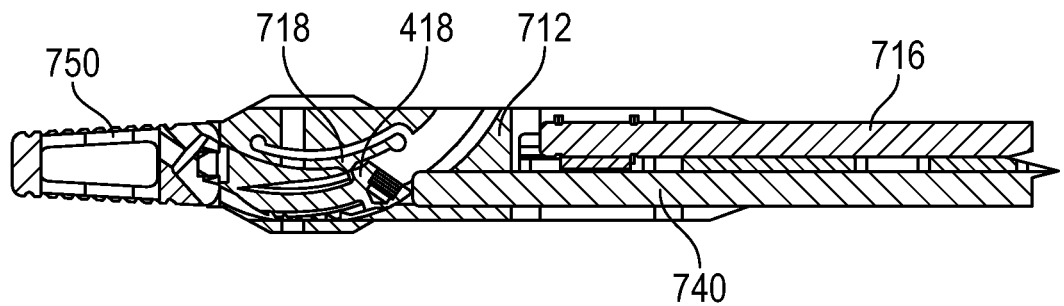
FIG. 55 is a cross-section view of the installation assembly of FIG. 52 according to an example embodiment.
Figure 56:
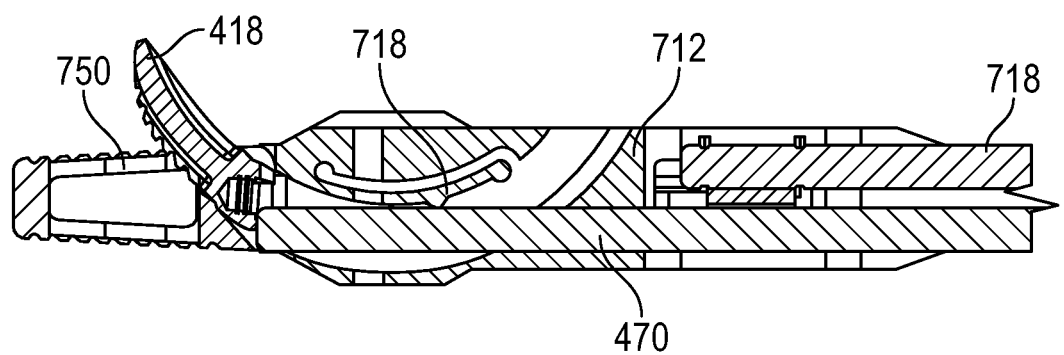
FIG. 56 is a cross section view of an installation assembly according to an example embodiment.

Referring now to FIGS. 55 and 56, another cross sectional view of the installation tool 700 is shown. In this example embodiment, the implant 750 is secured to the installation tool 700. As shown in FIG. 55, a bone barb 418 may be positioned within the interface body 712. In this example embodiment, the spring member 718 secures the bone barb 418 within the interface body. However, it should be appreciated that, in other embodiments, other types of springs and biasing members may be used to retain the bone barb 418 within the interface body 712. Once the implant 750 is positioned in a desired location, a drive member may be used to drive bone barbs 418 into adjacent bones. For example, in an example embodiment, the drive member may be an impactor 740. In this embodiment, the impactor 740 may be used to drive bone barbs 418 into adjacent bones. In this example embodiment, the spring member 718 generally prevents the bone barb 418 from moving within the interface body 712, however, the impactor 740 may apply a force to the bone barb 418 sufficient to release the bone barb 418 from the spring member 718. Then, the impactor 740 may be used to drive the bone barb 418 into a bone adjacent the implant 750.

In alternative embodiments, the drive member may be an actuator. For example, in certain embodiments, the drive member may be a threaded actuator. Alternatively, the drive member may be a manual actuator, a pneumatic actuator, a hydraulic actuator, an electric actuator, a spring-based actuator, or a motorized actuator. Further, the drive member may be a mechanical mechanism, such as a lever, a mallet, a screw, etc.

Figure 57:
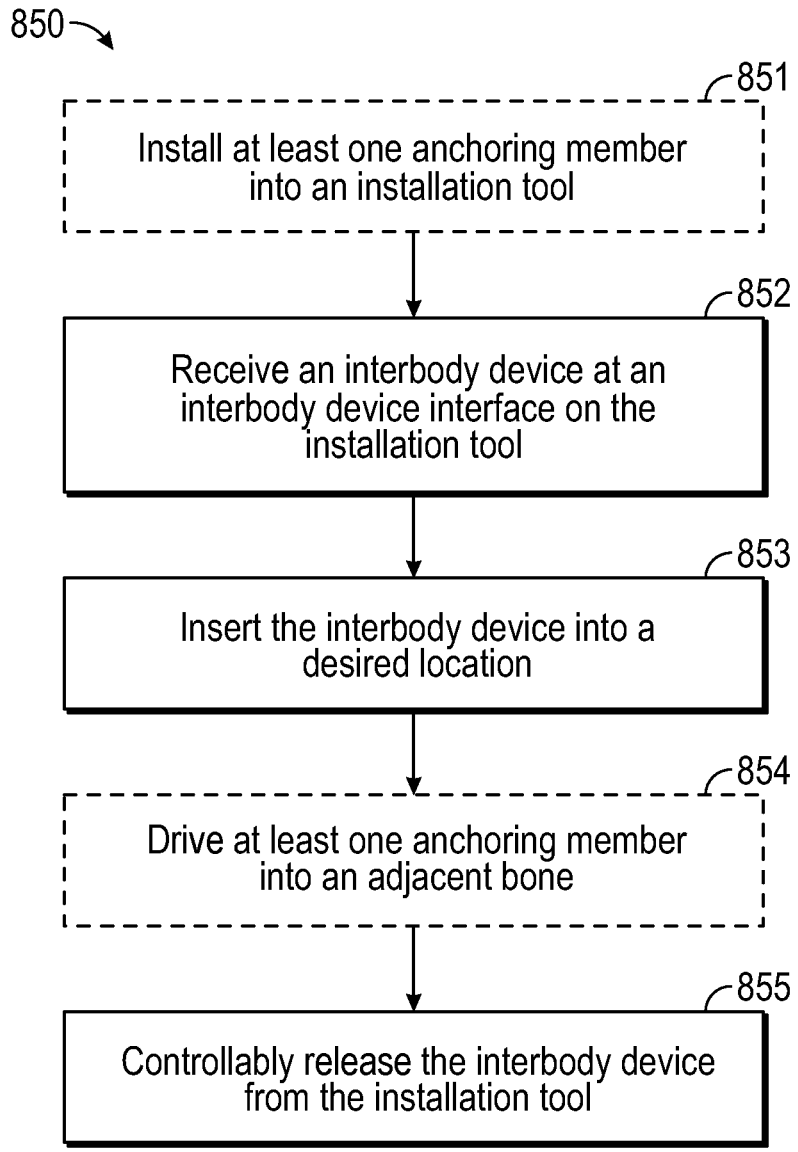
FIG. 57 is a flow diagram representation of a method of installing an interbody device according to an example embodiment.

Referring now to FIG. 57, a flow diagram representation of a method 850 of installing an interbody device is shown according to one embodiment. In the method 850, the boxes represented with dashed lines (e.g. 851, 854) are optional steps, depending on whether an anchoring member, such as a bone barb 418, is utilized in the installation process. In further embodiments, other steps may be omitted and/or added to the method. It should be noted that the order of the steps depicts an exemplary method, however, the steps do not need to be performed in this order, as will be made clear below.

At step 851, at least one anchoring member is installed into an installation tool. For example, this step may involve loading a bone barb 418 into the interface body 712, as shown in FIG. 55. In certain embodiments, the bone barb 418 is secured in place by the spring member 718, as shown in FIG. 55, until the bone barb 418 is driven out of the interface body 712 by the impactor 740, as shown in FIG. 56. In certain embodiments, the anchoring member, such as a bone barb 416, may be loaded into the interface body 412 through the interface face 713. In other embodiments, the interface body 712 may have slots on the top and/or bottom surface of the interface body 712 that are configured to receive anchoring members, such as a bone barb 416. In other embodiment, the implant 750 may secured to the interface face 713, and the anchoring members may then subsequently be loaded through the implant 750 and into the interface body 712. In further embodiments, the installation tool 700 may be loaded with anchoring members using any combination of the methods described above. It should be noted that step 851 need not necessarily be performed first, as will be discussed further herein.

At step 852, an interbody device, or an implant, is received at an interface face of an interface body of an installation tool. In an example embodiment, this step may involve using the control shaft 416 to adjust the arms 714, 715 into an open position, such as the position shown in FIG. 53. The implant 750 may then be received by the interface face 713. In certain embodiments, the implant 750 may then be secured by the arms 714, 715, as described above.

At step 853, an interbody device, or an implant, is inserted into a desired location in a patient. For example, in certain embodiments, an incision is made on the left side of the abdomen and the abdominal muscles are retracted to the side. The abdominal contents lay inside a large sack (peritoneum) that can also be retracted, thus allowing the spine surgeon access to the front of the spine without actually entering the abdomen. The interbody device, or implant 750, may then, for example, be inserted between two adjacent lumbar vertebrae. However, the implant may be placed into a desired location using any number of surgical methods.

At step 854, at least one anchoring member, such as a bone barb, is driven into an adjacent bone. In certain embodiments, an impactor 740 may be received within the installation tool 700, as shown in FIG. 55. The impactor 740 may then be used to drive the bone barb 418 out of the installation tool 700 and into an adjacent bone. In certain embodiments, the implant 750 may be configured to receive a plurality of anchoring members, such as bone barbs 418. For example, the implant 750 may be configured to receive three bone barbs 418. In this example, in step 851, three bone barbs 418 may be loaded into the installation tool 700. Step 851, which involves loading the anchoring members into the installation tool 700, may be performed before step 852, after step 852, after step 853, or after step 853. During step 854, the anchoring members may be driven into the adjacent bone individually or simultaneously. For example, if the implant 750 utilizes three anchoring members, such as bone barbs 418, all three bone barbs 418 may be driven into the adjacent bones at the same time using just one impactor 740, or using a plurality of impactors 740.

At step 855, an interbody device, or and implant, is controllably released from an installation tool. Once the implant 750 is inserted into a patient, and the implant 750 is secured to adjacent bones using anchoring members, the implant 750 may be released from the installation tool 700 so that the installation tool 700 may be removed from the patient. In example embodiments, releasing the implant 750 from the installation tool 700 may involve turning a control shaft 716 to move the arms into an open position, as described above.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure. Furthermore, the various embodiments disclosed herein may share certain features (e.g., a same or similar bone screw, screw retention mechanism, implant shape, etc.) with the implants disclosed in U.S. Publication No. 2017/0224502, which is incorporated herein by reference in its entirety.

What is claimed:

1. An implant comprising:
   an interbody device having a front, a rear, a first lateral side, a second lateral side, a central cavity, and a plurality of angled bores extending into the rear of the interbody device;
   wherein each angled bore is configured to receive an arced anchoring member, and
   wherein each arced anchoring member comprises:
   a shaft having a first end and a second end;
   a tip at the first end of the shaft; and
   a head at the second end of the shaft, the head comprising a flat surface, a threaded bore extending into the flat surface, and a rounded shoulder, wherein the flat surface is configured to receive a force to move the arced anchoring member within the angled bore, the threaded bore is configured to receive a tool, and the rounded shoulder is configured to engage a surface of the angled bore to guide the arced anchoring member within the angled bore.

2. The implant of claim 1, wherein the interbody device includes a porous portion and a solid portion, wherein the solid portion at least partially surrounds the porous portion proximate the rear, first lateral side, and second lateral side.

3. The implant of claim 2, wherein the first lateral side includes a first lateral window extending through the solid portion and the second lateral side includes a second lateral window extending through the solid portion.

4. The implant of claim 3, wherein the first lateral window enables visualization of the porous portion through the first lateral window, and wherein the second lateral window enables visualization of the porous portion through the second lateral window.

5. The implant of claim 3, wherein the first lateral window comprises a plurality of first lateral windows and the second lateral window comprises a plurality of second lateral windows.

6. The implant of claim 2, wherein the porous portion comprises a plurality of hexagonal-shaped pores.

7. The implant of claim 1, further comprising an anchoring member retention component, wherein the interbody device includes an aperture configured to receive the anchoring member retention component such that the anchoring member retention component prevents backing out of the arced anchoring member.

8. The implant of claim 7, wherein the anchoring member retention component is a cam screw having a head, a threaded shaft, a tip, and a shoulder.

9. The implant of claim 8, wherein the cam screw is movable between a first position, enabling insertion and removal of one of the arced anchoring member, and a second position, preventing back out of one of the arced anchoring member.

10. The implant of claim 1, further comprising the arced anchoring member, wherein the arced anchoring member comprises a bone barb.

11. An implant comprising:
    a plurality of arced anchoring members; and
    an interbody device having a front, a rear, a first lateral side, a second lateral side, a central cavity, and a plurality of arced angled bores each configured to receive one of the plurality of arced anchoring members;
    wherein the interbody device includes a porous portion and a solid portion at least partially surrounding the porous portion proximate the rear, first lateral side, and second lateral side, the solid portion having a higher density than the porous portion, and
    wherein each arced anchoring member comprises:
    a shaft having a first end and a second end;
    a tip at the first end of the shaft; and
    a head at the second end of the shaft, the head comprising a flat surface, a threaded bore extending into the flat surface, and a rounded shoulder, wherein the flat surface is configured to receive a force to move the arced anchoring member within the angled bore, the threaded bore is configured to receive a tool, and the rounded shoulder is configured to engage a surface of the angled bore to guide the arced anchoring member within the angled bore.

12. The implant of claim 11, wherein the first lateral side includes a first lateral window extending through the solid portion and the second lateral side includes a second lateral window extending through the solid portion, and wherein the interbody device is a single integral piece.

13. The implant of claim 12, wherein the first lateral window enables visualization of the porous portion through the first lateral window, and wherein the second lateral window enables visualization of the porous portion through the second lateral window.

14. The implant of claim 13, wherein the first lateral window comprises a plurality of first lateral windows and the second lateral window comprises a plurality of second lateral windows.

15. The implant of claim 12, further comprising an anchoring member retention component, wherein the interbody device includes a threaded hole configured to receive the anchoring member retention component, wherein the anchoring member retention component is a cam screw having a head, a threaded shaft, a tip, and a shoulder.

16. The implant of claim 15, wherein the cam screw is movable between a first position, enabling insertion and removal of one of the plurality of arced anchoring members, and a second position, preventing back out of one of the plurality of arced anchoring members.

17. An implant system comprising:
an implant body comprising:
  a bore configured to receive an arced anchoring member; and
  an installation tool interface, wherein the arced anchoring member comprises:
    a shaft having a first end and a second end;
    a tip at the first end of the shaft; and
    a head at the second end of the shaft, the head comprising a flat surface, a threaded bore extending into the flat surface, and a rounded shoulder, wherein the flat surface is configured to receive a force to move the arced anchoring member within the bore, the threaded bore is configured to receive a tool, and the rounded shoulder is configured to engage a surface of the bore to guide the arced anchoring member within the bore; and
an installation tool comprising:
  an interface body configured to engage the installation tool interface;
  an arced bore configured to receive the arced anchoring member.

18. The implant system of claim 17, further comprises a plurality of arced anchoring members, including the arced anchoring member, wherein the installation tool further comprises:
  a plurality of installation bores configured to simultaneously receive a plurality of drive members; and
  the plurality of drive members configured to drive the plurality of arced anchoring members while the installation tool is attached to the implant body.

19. The implant system of claim 18, wherein the plurality of drive members are usable to simultaneously drive the plurality of arced anchoring members into an adjacent bone.

20. The implant system of claim 19, wherein the arced anchoring member comprises a bone barb configured to be inserted into the adjacent bone, wherein the bone barb defines a curved shaft configured to translate within the arced bore.

* * * * *